(12) United States Patent
Fateh

(10) Patent No.: US 6,364,485 B1
(45) Date of Patent: *Apr. 2, 2002

(54) METHODS AND SYSTEMS FOR RELIEVING EYE STRAIN

(75) Inventor: Sina Fateh, Sunnyvale, CA (US)

(73) Assignee: Vega Vista, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/310,901

(22) Filed: May 12, 1999

Related U.S. Application Data

(63) Continuation-in-part of application No. 08/902,432, filed on Jul. 29, 1997, now Pat. No. 6,042,231.
(60) Provisional application No. 60/023,066, filed on Aug. 2, 1996.

(51) Int. Cl.[7] ................................................ A61B 3/00
(52) U.S. Cl. ...................................... 351/203; 345/619
(58) Field of Search ............................... 345/326, 121, 345/115, 127, 660, 672, 619; 351/200, 201, 203

(56) References Cited

U.S. PATENT DOCUMENTS

| | | |
|---|---|---|
| 2,270,069 A | 1/1942 | Martin |
| 2,362,588 A | 11/1944 | Sheppard ........................ 88/20 |
| 3,388,646 A | 6/1968 | Sullivan |
| 3,468,545 A | 9/1969 | Anderson |
| 3,582,189 A | 6/1971 | Moritz et al. |
| 3,917,278 A | 11/1975 | Steinman, Jr. |
| 4,067,129 A | 1/1978 | Abramson et al. |
| 4,068,230 A | 1/1978 | Schneiter |
| 4,137,566 A | 1/1979 | Hass et al. |
| 4,294,522 A | 10/1981 | Jacobs ........................... 351/2 |
| 4,365,873 A | 12/1982 | Ginsburg |
| 4,611,893 A | 9/1986 | Schrier |

(List continued on next page.)

FOREIGN PATENT DOCUMENTS

| | | |
|---|---|---|
| EP | 0 411 821 | 7/1990 |
| EP | 0411821 A1 | 2/1991 |
| FR | 2029221 | 10/1970 |
| FR | 2 029 221 | 10/1970 |
| FR | 2 737 108 | 7/1995 |
| FR | 2737108 A1 | 1/1997 |
| WO | WO98/05251 A1 | 2/1998 |

OTHER PUBLICATIONS

Dr. Roger R. Gagnon; EyeWorks 1.0; Software Manual; ICC Group Inc. 1995.

(List continued on next page.)

Primary Examiner—Kent Chang
(74) Attorney, Agent, or Firm—Oppenheimer Wolff & Donnelly

(57) ABSTRACT

The methods and systems of the present invention enable a user to perform eye exercises and training that may aid in relieving eye fatigue and eye strain. In general, the present invention teaches providing movement between associated images having a plurality of objects. When a viewer focuses on a central focal point interposed between the viewer's eyes and the associated images, the viewer perceives, in addition to the associated images, a merged image (also possibly having a plurality of objects) derived from the associated images. Then, by performing one of a number of suitable movements with the associated objects, the viewer's eyes are exercised. For example, by increasing the separation between the associated images along a horizontal axis while the viewer attempts to maintain the perception of the merged image, the viewer's eyes are exercised in such a manner that eye fatigue and eye strain may be relieved. The present invention further teaches a computer input device that has an ocular device incorporated therein. The ocular device has a stem, which in some cases is telescopic, and a focal tip. A viewer may utilize the ocular device to perform certain eye exercises.

32 Claims, 16 Drawing Sheets

U.S. PATENT DOCUMENTS

| | | |
|---|---|---|
| 4,716,469 A | 12/1987 | Kim et al. |
| 4,831,448 A | 5/1989 | Park |
| 4,944,572 A | 7/1990 | Young |
| 5,026,151 A | 6/1991 | Waltuck et al. |
| 5,051,931 A | 9/1991 | Cheu et al. |
| 5,252,950 A | 10/1993 | Saunders et al. |
| 5,289,220 A | 2/1994 | Fidler et al. |
| 5,311,220 A | 5/1994 | Eichenlaub |
| 5,322,441 A | 6/1994 | Lewis et al. |
| 5,351,963 A | 10/1994 | Baek |
| 5,442,734 A | 8/1995 | Murakami et al. .......... 395/127 |
| 5,452,516 A | 9/1995 | Schegerin |
| 5,510,893 A | 4/1996 | Suzuki |
| 5,515,069 A | 5/1996 | Dillon, III. |
| 5,570,301 A | 10/1996 | Barrus |
| 5,579,026 A | 11/1996 | Tabata ........................... 345/8 |
| D376,648 S | 12/1996 | Fateh |
| 5,661,539 A | 8/1997 | Sheedy |
| 5,668,622 A | 9/1997 | Charbonnier et al. |
| 5,686,940 A | 11/1997 | Kuga |
| 5,777,715 A | 7/1998 | Kruegle et al. ............. 351/158 |
| 6,075,525 A * | 6/2000 | Hsieh .......................... 345/326 |

OTHER PUBLICATIONS

Orthoptic Treatment; Chapter 18, pp. 178–201.

James E. Sheedy, O. D. PhD.; Solving Vision Problems at Computers in the United States; Health and Vision, Points De Vue N 33, Oct. 1995.

The Solution to Computer Eyestrain; Latest Press Materials; Prio Corporation; http://www.prio.com, Jun. 13, 1997.

A Vision Therapy Software–Eyeworks; If you work on your computer more than 1 hour at a time, you need Eyeworks; Jul. 25, 1996.

PCT International Search Report, International Application No.: PCT/US97/12945 filed Jul. 29, 1997, mailed Dec. 19, 1997, 4 pages.

EPO Supplementary European Search Report, Application No.: EP97935092, 3 pages.

PCT Request for FATHP001.P dated Jul. 29, 1997, 4 pages.

* cited by examiner

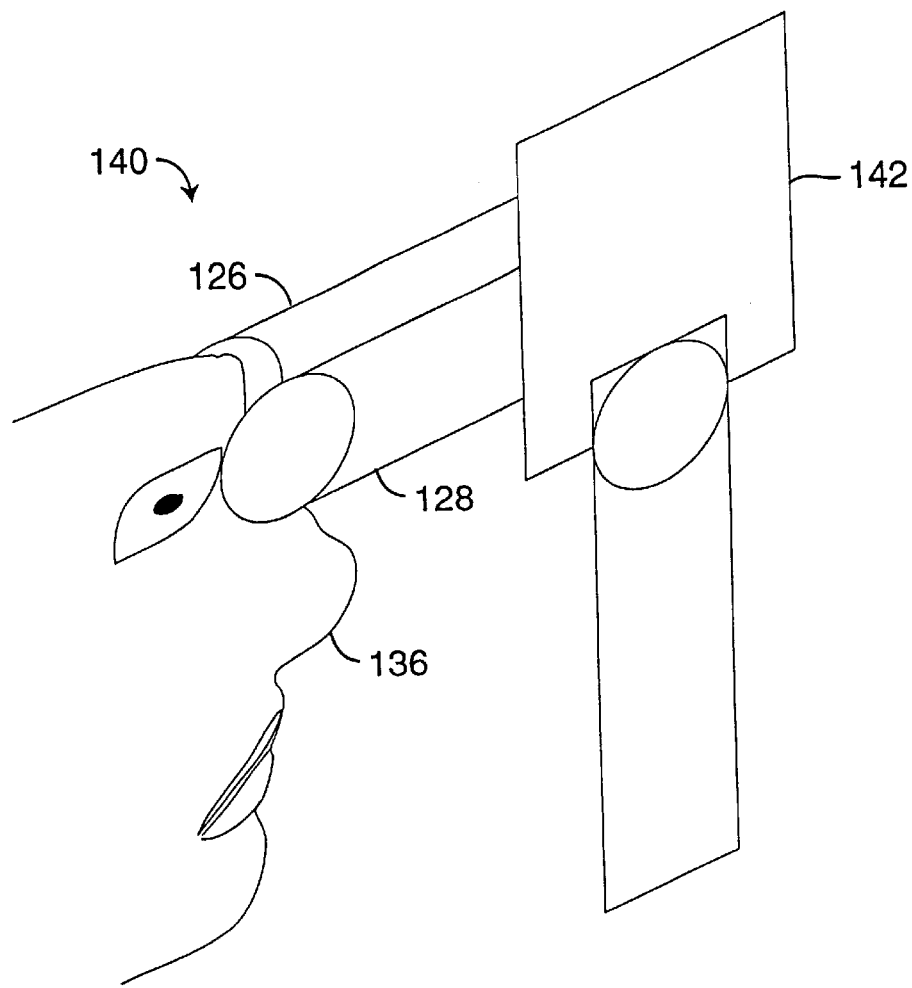
Figure 2(a)
(Prior art)
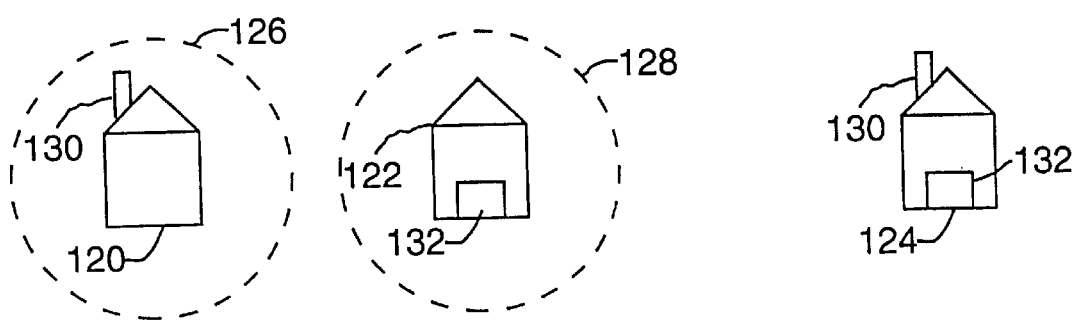
Figure 2(b)
(Prior art)
Figure 2(c)
(Prior art)

Figure 5(a)
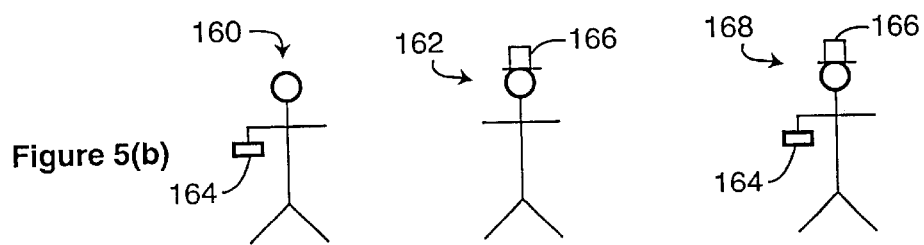
Figure 5(b)
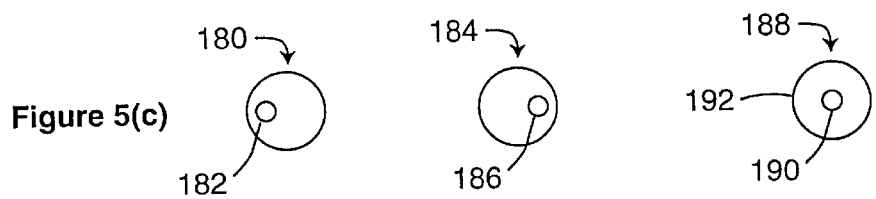
Figure 5(c)
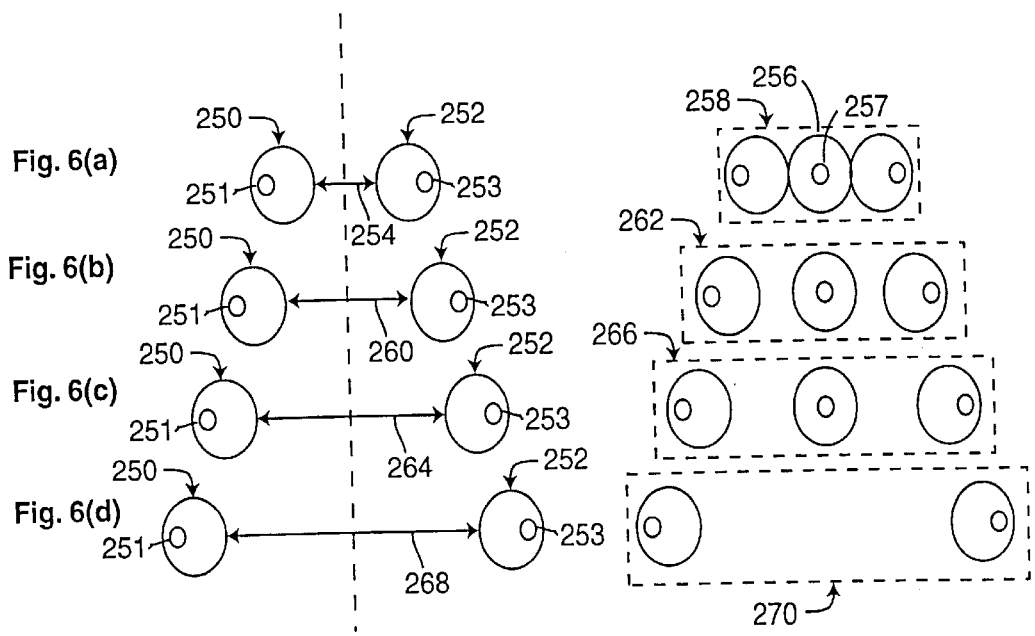
Fig. 6(a)
Fig. 6(b)
Fig. 6(c)
Fig. 6(d)

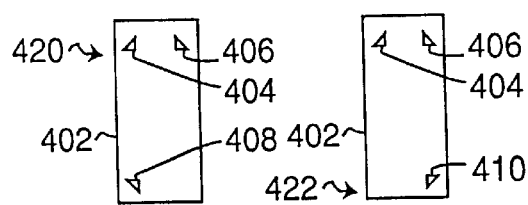 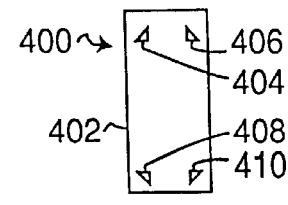
Figure 7(a)
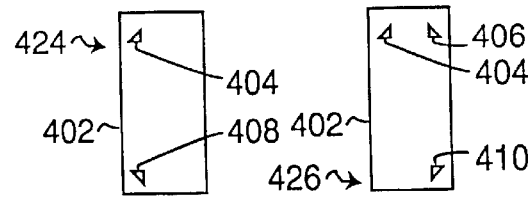 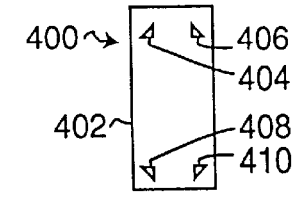
Figure 7(b)
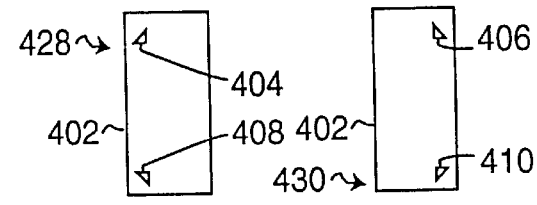 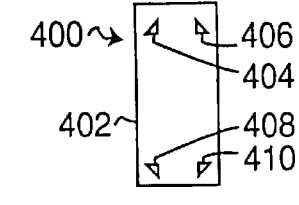
Figure 7(c)
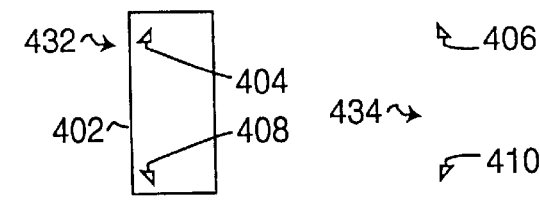 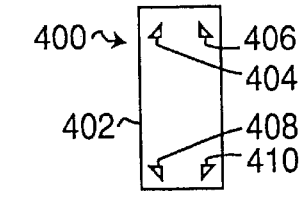
Figure 7(d)

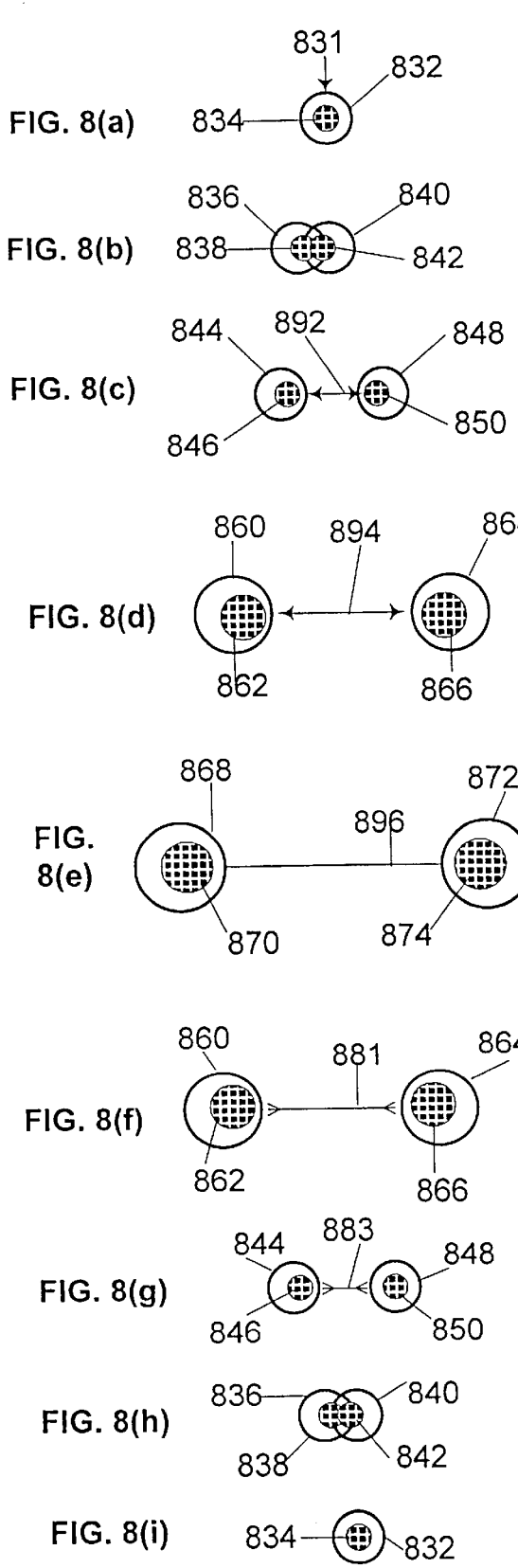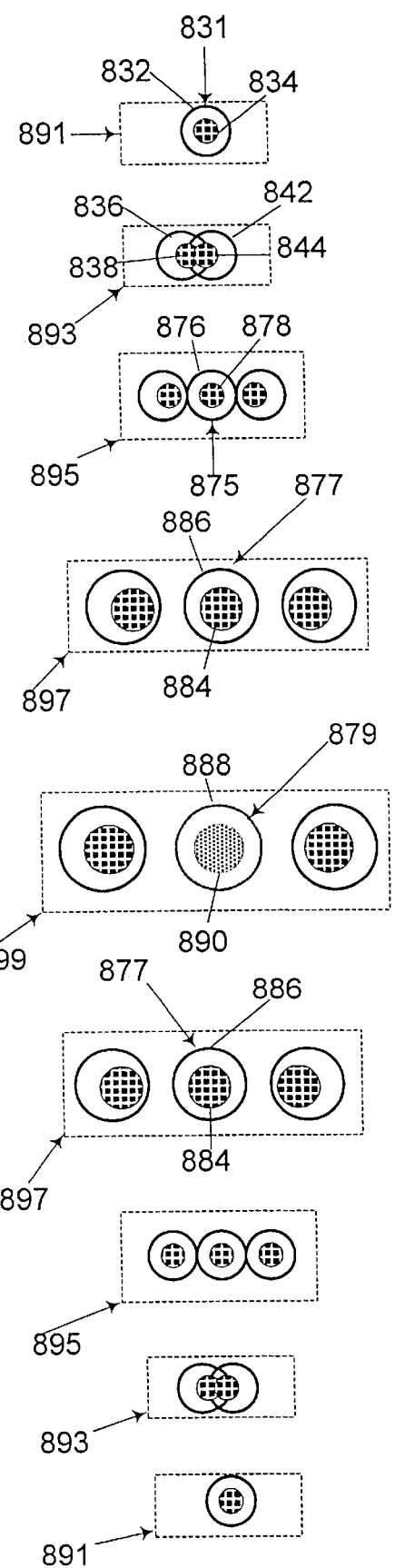

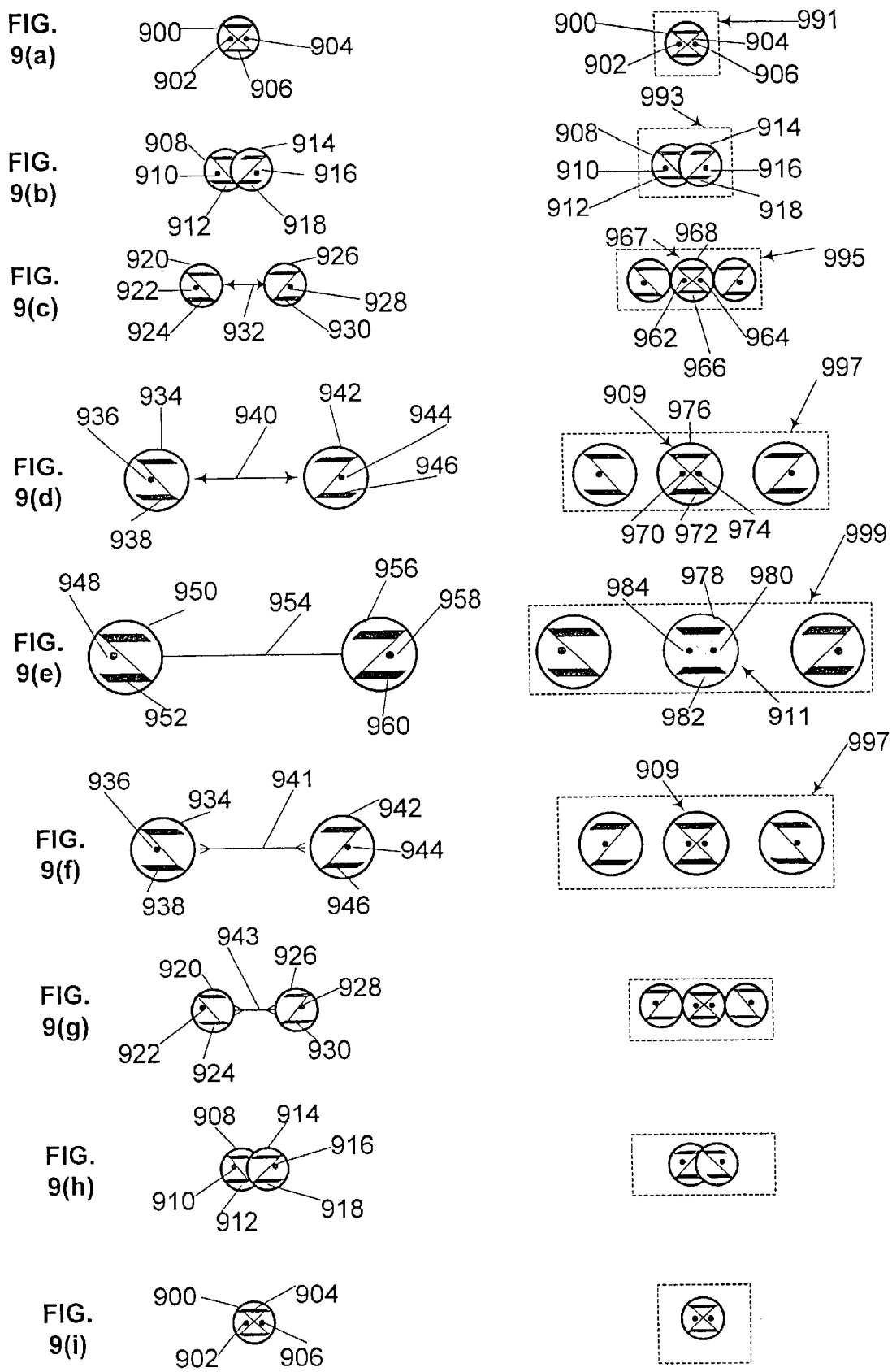

METHODS AND SYSTEMS FOR RELIEVING EYE STRAIN

CROSS-REFERENCE TO RELATED APPLICATION

This application is a continuation-in-part of Fateh's copending U.S. application Ser. No. 08/902,432, entitled "Methods and Systems for Relieving Eye Strain," filed on Jul. 29, 1997, now U.S. Pat. No. 6,042,231, which claims the benefit of U.S. Provisional Application Serial No. 60/023,066, entitled "METHODS AND SYSTEMS FOR RELIEVING EYE STRAIN," filed Aug. 2, 1996, both of which are incorporated herein in their entirety.

TECHNICAL FIELD

The present invention relates to the field of orthoptic treatment. More specifically, the present invention teaches methods and systems for use in exercising eye muscles, especially for the relief and prevention of eye strain.

BACKGROUND

A growing proportion of the population in the industrialized world spends time performing tasks that are known to cause eye fatigue and/or eye strain. Office workers increasingly are required to work at computer terminals to perform tasks such as word processing, data entry, and generating computer graphics. Students and children are using computers for study and in the classroom. Even at home, computers and televisions are commonly viewed for entertainment and information purposes. Thus, it comes as no surprise that an increasing number of people in the industrialized world are seeking relief from discomfort and decreased vision due to eye strain.

The human eye includes various muscles which, like any part of the human body, will tire and strain when kept in a fixed configuration for sufficiently long periods. Immediate symptoms of eye fatigue and eye strain include headaches and difficulty focusing one's vision. In the long term, prolonged or severe eye fatigue and strain may decrease the strength of eye muscles and require corrective lenses (or an increased prescription for those already requiring corrective lenses).

Some of the most common causes of eye fatigue and/or strain include viewing close objects, viewing objects displayed on a light emitting medium, and simply viewing images for excessive time periods. By way of example, a typical computer user may spend hours viewing a computer display screen while performing computer-related tasks. The light emitting display screen forces the computer user's eyes to constantly adjust, while simultaneously diminishing the eyes movement which normally helps the eyes to stretch and relax and thereby relieve eye fatigue and eye strain. Furthermore, objects being viewed on the display screen are often close enough to the viewer to cause the viewer's eye difficulty in maintaining a clear focus on the objects, possibly causing eye strain and fatigue. As will be appreciated, the effects of such causes on a particular viewer vary depending upon the visual abilities of that particular viewer.

When an object is too close to a viewer, the viewer is forced to bring her eyes inward (towards her nose). The motion of the eyes turning inward is called convergence. Convergence requires intensive exertion of the eye muscles, in particular the ocular muscles. When the eyes are not properly relaxed through either visual exercise or rest, the viewer may experience eye fatigue and/or eye strain. Repeated and/or prolonged convergence can permanently decrease the strength of the eye muscles.

In addition, a viewer's eyes must focus in order to properly perceive an object. Focusing causes strain to the viewer's eyes. In order to focus on close objects, the eye's lens thickens. That is, the closer an object to the viewer, the thicker the eye's lens must shape themselves. Thickening the eye's lens is particularly exhausting on the eye muscles, serving to exacerbate the fatigue and strain brought on by the convergence that also accompanies viewing close objects.

One result of eye fatigue and eye strain is a diminished synchronization between a viewer's pair of eyes. That is, the viewer's left and right eyes are not working synchronously to provide the visual information required to visually perceive one's surroundings. Accordingly, common orthoptic tests involve monitoring the eye's ability to synchronize, while common orthoptic treatments involve the viewer performing eye exercises that promote synchronization, either through stretching and strengthening the eye muscles, or via forced relaxation.

FIG. 1 illustrates an orthoptical exercise method 100 commonly performed with a synoptophore by optometrists (or other medical professionals), together with their patients, to examine and promote eye synchronization. The method 100 begins in a step 102 involving any initialization requirements. These depend, in part, upon the equipment being used. However, in general, a viewer (i.e., the patient) places their face over the viewing portion of eye synchronization test equipment such that each eye is looking into an individual scope. Once the viewer is prepared, a step 104 displays two associated images, one in each scope. Typically, the two associated images are not identical, but have many common portions. After the two associated images are displayed, in a step 106 the viewer focuses the two images into a single perceived "merged" image. In general, the merged image is a mapping of the two associated images. In a simple case, the single perceived merged image will replicate all the common portions of the associated images, as well as each of the associated images' unique portions. An example of a single perceived merged image of this type is described below in reference to FIGS. 2(b) and 2(c). In other cases, however, the single perceived image might replicate all the common portions but create a portion perceived as three dimensional out of the associated images' unique portions. This is due to the operation of the viewer's eyes intended to provide stereoscopic vision. As will be appreciated, "stereoscopic vision" is the ability to perceive distance and the three dimensional properties of a viewed object.

Once the viewer has focused on a single perceived merged image, it is determined in a step 108 whether the method 100 is done. For example, has the viewer completed his or her exercises, or has the optometrist completed the tests? If so, then the method is complete in a step 110. If the method 100 is not complete, then step 108 passes control to a step 112. In a step 112, the optometrist manually adjusts the two associated images along the horizontal plane, disrupting the viewer's focus and thereby causing the viewer to once again perceive the two associated images as distinct and not one single perceived merged image. After step 112, the method 100 loops back to step 106 where, once again, the viewer is allowed to focus the two images into a single perceived merged image.

FIG. 2(a) illustrates a patient 136 utilizing a synoptophore 140 suitable for performing the method 100 of FIG. 1. The synoptophore includes a left scope 126 and a right scope 128 coupled with a viewing screen 142. The patient 136 places her face up against the synoptophore 140 such that the patient's left and right eyes are directly in front of the left scope 126 and the right scope 128, respectively. Two associated images, such as those described above with reference to FIG. 1, are displayed by the viewing screen 142, one in each scope. As described above, the patient 136 then focuses her eyes to perceive a single, merged image.

With reference now to FIGS. 2(b) and 2(c), a specific example of two associated stick house images 120 and 122 along with a perceived merged image 124 will be described. Broken lines represent the left scope 126 and right scope 128 of the synoptophore 140 described above with reference to FIG. 2(a). Thus, a viewer gazing only into the left scope 126 would perceive just the image 120. Similarly, a viewer gazing only into the right scope 128 would perceive just the image 122. However, a viewer gazing into both scopes appropriately would initially see both images, as described above with reference to steps 104 and 106 of FIG. 1. Then, as described above with reference to step 106 of FIG. 1, the viewer would begin to focus and shortly thereafter perceive just the single merged image 124 of FIG. 2(b). Note that a chimney portion 130, only presented in the image 120, and a doorway portion 132, only presented in the image 132, are both perceived by the viewer in the single perceived merged image 124.

While the method 100 is useful in testing and promoting eye synchronization, it has a number of drawbacks. For example, imprecise operation by the optometrist decreases the effectiveness that the method 100 has upon eye strain and fatigue. Flaws such as asynchronous movement of the associated images, including substantially discrete jumps and differing average speeds, serve to prevent the patient from obtaining the optimal benefit. In addition, these methods must be performed in a doctor's office or with the aid of equipment and assistance that are not easily provided in the very environments where the eye strain and eye fatigue is being experienced. Thus, sufferers of eye strain and fatigue must travel to doctors' offices for expensive and lengthy treatments.

It would be advantageous to provide methods and systems that overcome the above-described drawbacks with current treatments for eye strain and eye fatigue. In particular, it would be advantageous to provide systems and methods that provide highly synchronized, smooth motion of images for eye training. In addition, it would be advantageous to provide systems and methods for treating and/or preventing eye strain and eye fatigue that can be performed locally and without extensive apparatus or manual assistance.

SUMMARY OF THE INVENTION

To achieve the foregoing and other objectives and in accordance with the purpose of the present invention, methods and systems for relieving eye strain are taught. According to one aspect of the present invention, a method for relieving eye strain of a viewer's eyes includes three steps. First, two associated images are displayed on a display screen laterally separated along a horizontal line. A viewer focusing on a central focal point interposed between the viewer's eyes and the associated images, will perceive, in addition to the associated images, a merged image derived from the associated images. Next, an input is received indicating that the viewer perceives the merged image. Then, the associated images are moved in such a manner that the viewer's eyes are exercised when the viewer attempts to maintain perception of the merged image.

In one related aspect, the method further includes stopping the movement of the associated images in response to an indication that the viewer no longer perceives the merged image. In another related aspect, statistical information concerning the viewer's eye exercises, perhaps including or based upon historical data, is provided to the viewer. In still another related aspect, the viewer is allowed to select parameters defining, at least in part, the nature of a specific eye exercise to be performed.

In another related aspect of the present invention, the viewer is provided a free standing apparatus having a focal tip that may be positioned to intersect with the central focal point. This aids the viewer in focusing upon the central focal point. In one specific embodiment, the free standing apparatus has a base and a telescopic stem. The telescopic stem has a number of sections that slide one inside of another thereby allowing the telescopic stem to extend and contract. The telescopic stem is attached to the base by a hinge enabling the telescopic stem and the base to fold together. The focal tip is located on a distal end of the telescopic stem with respect to the base.

A second aspect of the present invention teaches a screen saver method executed upon a computer system having a display screen. In response to a first predefined event such as nonuse of the computer, the method executes a screen saver operable to decrease damage to the display screen. In response to a second predefined event such as the user returning to use of the computer, the method queries the user whether the user desires to perform eye exercises. If so, the method performs the following. First, two associated images are displayed on a display screen laterally separated along a horizontal line. When a viewer focuses on a central focal point interposed between the viewer's eyes and the associated images, the viewer perceives, in addition to the associated images, a merged image derived from the associated images. Next, an input is received indicating that the viewer perceives the merged image. Then, the associated images are moved in such a manner that the viewer's eyes are exercised.

One embodiment of the present invention teaches a system for relieving eyestrain of a viewer's eyes. The system includes a CPU, a RAM, a ROM, a display screen coupled to the CPU, an input device coupled with the CPU, and an eye exercise application implemented upon the computer system. The eye exercise application is operable to display two associated images on the display screen having a lateral separation distance along a horizontal line. When a viewer focuses on a central focal point interposed between the viewer's eyes and the associated images, the viewer perceives, in addition to the associated images, a merged image derived from the associated images. The eye exercise application is further operable both to receive an input indicating that the viewer perceives the merged image and to move the associated images in such a manner that the viewer's eyes are exercised.

Yet another embodiment of the present invention teaches a computer program stored on a computer readable medium, the computer program having computer executable instructions. Still another embodiment of the present invention teaches a computer data signal embodied in a carrier wave representing computer executable instructions. For both, the computer executable instructions perform the following. First, two associated images are displayed on a display screen laterally separated along a horizontal line. When a viewer focuses on a central focal point interposed between the viewer's eyes and the associated images, the viewer perceives, in addition to the associated images, a merged image derived from the associated images. Next, an input is received indicating that the viewer perceives the merged image. Then, the associated images are moved in such a manner that the viewer's eyes are exercised.

Still another embodiment of the present invention teaches a computer input device having an ocular device. Suitable forms for the computer input device include a mouse pointing device, a trackball pointing device, and a keyboard. The ocular device has a stem and a focal tip and is well suited for use by a viewer to perform certain eye exercises. In related embodiments, the stem is telescopic and connected to the computer input device by way of a hinge. This enables the ocular device to contract and fold into the computer input device. In other related embodiments, the computer input device further includes a position sensor operable to measure the distance from the viewer to the computer input device. Additional embodiments have a button which when engaged transmits a signal to a connected computer system indicating that eye exercise software should be executed upon the computer system.

BRIEF DESCRIPTION OF THE DRAWINGS

The invention, together with further objectives and advantages thereof, may best be understood by reference to the following description taken in conjunction with the accompanying drawings which are described below.

FIG. 2(a), of the prior art, is a pictorial illustration showing the visage of a viewer gazing into the scopes of the synchronization evaluator in order to view the associated images projected on the viewing screen;

FIG. 2(b), of the prior art, is a pictorial illustration showing two associated images as initially perceived by a patient performing the method of FIG. 1;

FIG. 2(c), of the prior art, is a pictorial illustration showing a merged image subsequently perceived by a patient performing the method of FIG. 1;

FIG. 5(a) is a pictorial illustration showing two associated images sharing no common objects, and the resultant merged image perceived by a viewer;

FIG. 5(b) is a pictorial illustration showing two associated images sharing common objects, and the resultant merged image perceived by a viewer;

FIG. 5(c) is a pictorial illustration showing two associated images sharing common objects, the dissimilar objects related such that the resultant merged image is perceived having three dimensional characteristics;

FIGS. 6(a), 6(b), 6(c), and 6(d) are diagrammatic illustrations successively showing the separation of a plurality of images in accordance with one embodiment of the present invention;

FIGS. 7(a), 7(b), 7(c), and 7(d) are a set of pictorial illustrations showing how different pairs of associated images may result in the perception of a single, identical, merged image;

FIG. 8(a)–8(i) are diagrammatic illustrations successively showing the separation of a plurality of images in accordance with one embodiment of the present invention;

FIG. 9(a)–9(i) are diagrammatic illustrations successively showing the separation of a plurality of images in accordance with one embodiment of the present invention;

BEST MODES FOR CARRYING OUT THE INVENTION

The methods and systems of the present invention enable a user to perform eye exercises and training that may aid in relieving eye fatigue and eye strain. In general, the present invention teaches providing movement between associated images having a plurality of objects. When a viewer focuses on a central focal point interposed between the viewer's eyes and the associated images, the viewer perceives, in addition to the associated images, a merged image (also possibly having a plurality of objects) derived from the associated images. Then, by performing one of a number of suitable movements with the associated objects, the viewer's eyes are exercised. For example, by increasing the separation between the associated images along a horizontal axis while the viewer attempts to maintain the perception of the merged image, the viewer's eyes are exercised in such a manner that eye fatigue and eye strain may be relieved.

Figure 1:
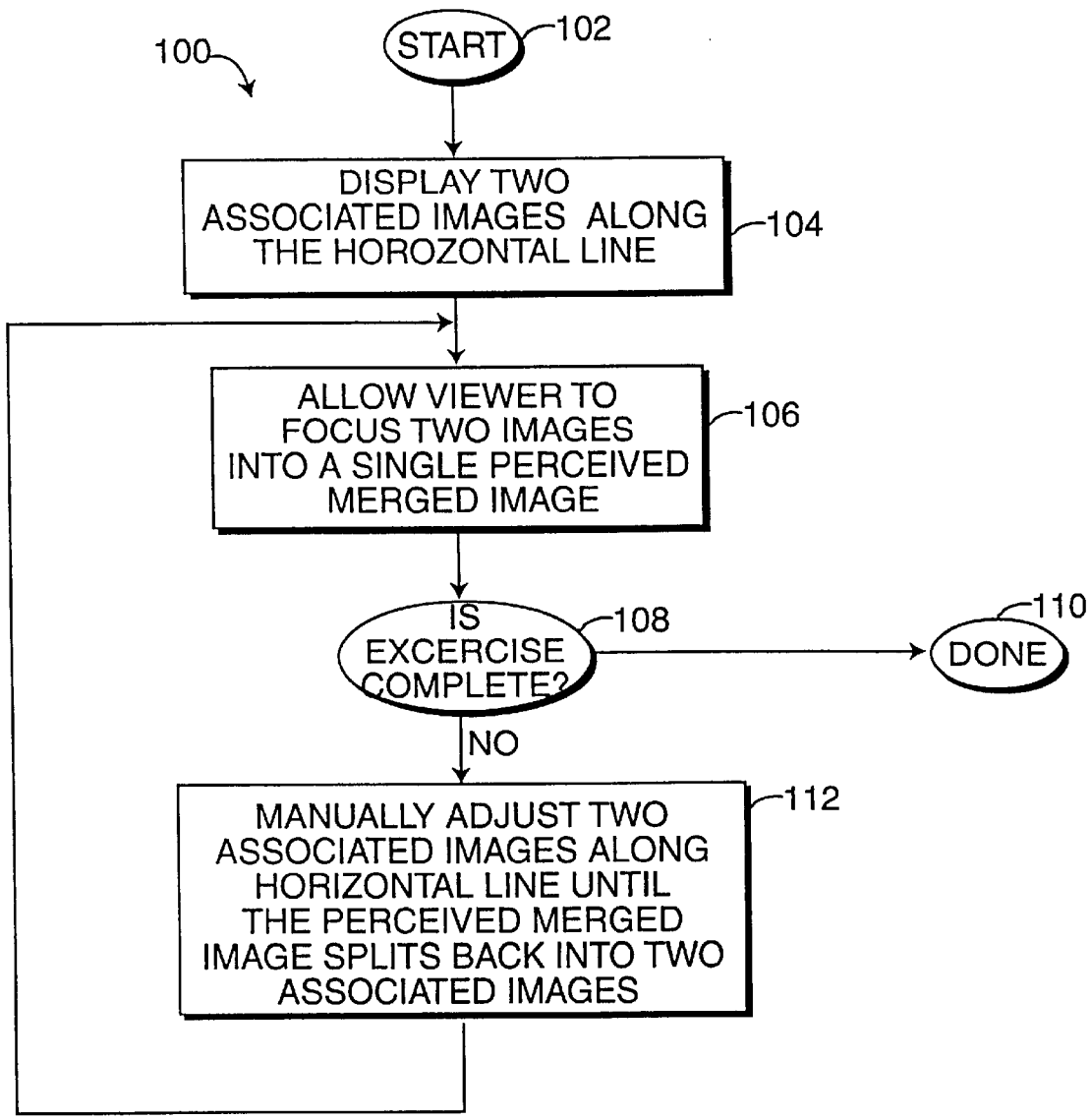
FIG. 1, of the prior art, is a flow chart showing a prior art method for examining and exercising a patient's eyes.
Figure 3:
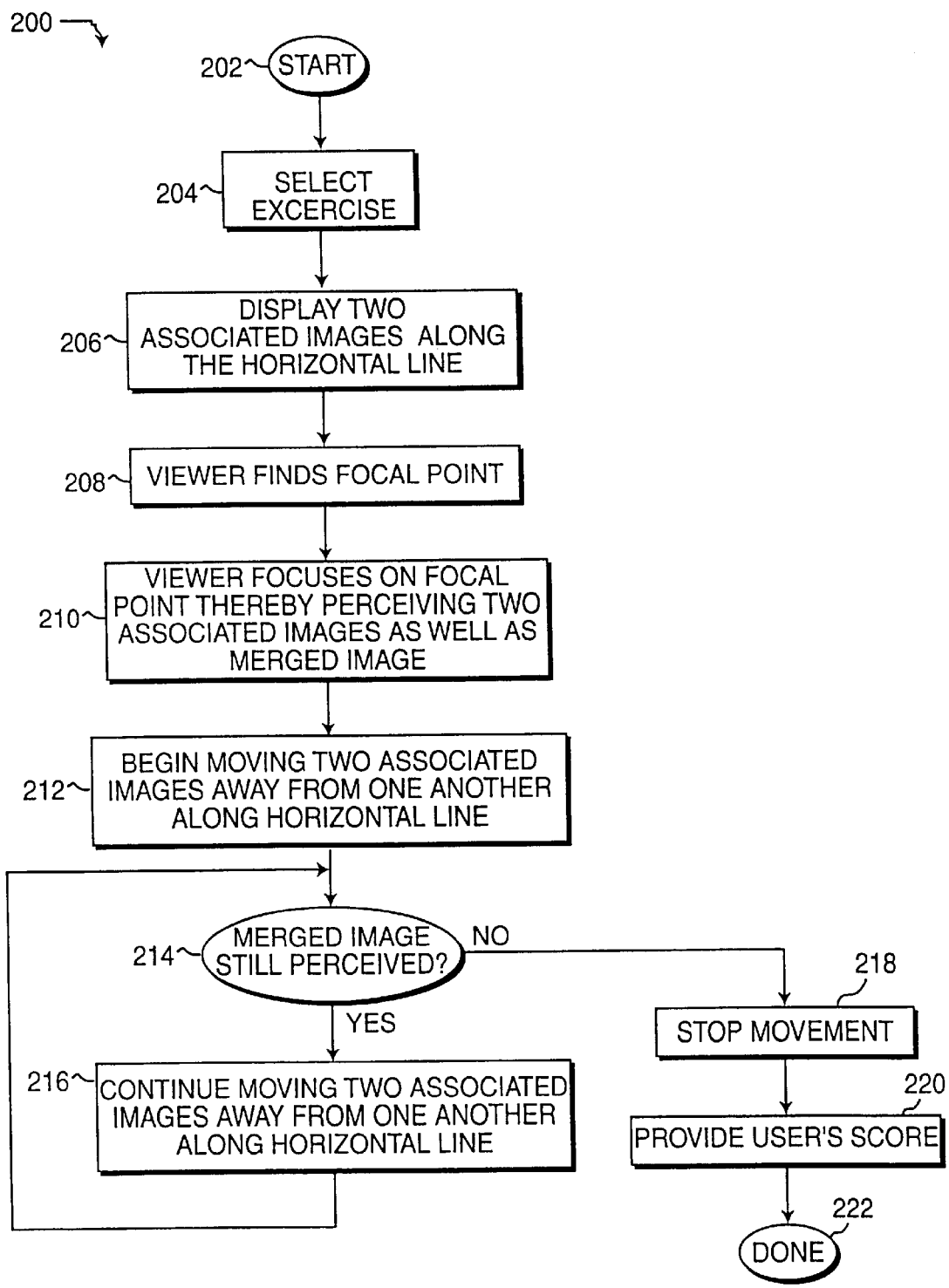
FIG. 3 is a flow chart showing one embodiment of a method in accordance with the present invention by which a viewer may exercise his or her eyes.

FIG. 3 is a flow chart illustrating an eye exercise method 200 in accordance with one aspect of the present invention. In a start step 202, the exercise method 200 begins. Step 200 includes any initialization processes required to prepare for the exercise method 200. For example, if the method 200 is implemented on a computer system, step 202 includes turning on the computer and executing the software that implements the method 200. Then, after initialization, a step 204 selects an appropriate and/or desired exercise. As will be described below in more detail with reference to FIGS. 4, 5 and 7, in some embodiments a viewer can select an exercise varying in difficulty and character. By way of example, parameters such as a selected images' perceived pattern, associated images separation speed, a starting separation distance of associated images, and an absolute image size are all suitable parameters for the viewer to manipulate. Separation speeds within the range of about 0.2 cm/sec to 0.5 cm/sec have been found to work well and are comfortable on the eyes. More preferably, the separation speed may be in the range of 0.3 cm/sec to 0.4 cm/sec. One suitable embodiment for the selecting exercises step 204 is described below with reference to FIG. 10. In any event, after step 204 a next step 206 displays two associated images along an axis running substantially horizontal relative to the user (the "horizontal line"), with the two associated images being separated by a predefined distance along the horizontal line.

After the two associated images are displayed, in a step 208 the viewer locates a central focal point of the two associated images. The central focal point lies between the viewer and the two associated images along a focal line. The focal line is approximately perpendicular to the horizontal line and intersects a point on the horizontal line that is approximately centered between the two associated images. The actual location of the central focal point will vary based upon the particular viewer and the characteristics of the associated images. By focusing on the focal point, in a step 210 the viewer will perceive a merged image in addition to the two associated images unless the strength of the viewer's eye muscles has deteriorated to such an extent as to prevent the necessary eye coordination required for merging the two displayed images. It will be appreciated that the viewer's ability to perceive the merged image will vary with the particular viewer's visual capabilities as well as his or her current level of eye fatigue and eye strain.

The nature of the merged image depends upon the two associated images. For example, the merged image might be a single object being a composite of the two associated images. However, the associated images could consist of multiple objects, in which case the merged image might itself consist of multiple objects formed from the associated images. In any event, the steps 208 and 210 may be performed by a variety of techniques. Some users will be able to simply view the associated images and then find and focus their eyes onto the central focal point, thereby obtaining the perception of the merged image. However, most viewers will find the provision of a physical marker overlapping the central focal point helpful. By focusing on the physical marker, the viewer is essentially focusing on the central focal point. The physical marker may take any suitable form such as the viewer's finger, a pencil held by the viewer, or, as described in more detail below with reference to FIGS. 12 and 12(a)–12(c), some type of free standing apparatus.

Once the viewer has perceived the merged image, a step 212 begins moving the two associated images apart from one another along the horizontal line. In some embodiments, the separation speed will be constant. However, it is contemplated that the separation speed could vary. In general, a faster separation speed corresponds to a higher difficulty level in perceiving the merged image. In preferred embodiments, the motion of the associated images is substantially smooth, e.g., no discrete jumps in acceleration are perceived by the viewer. The separation begun in step 212 may be initiated by any suitable method. In some embodiments, the viewer manually indicates perception of the merged image, thereby initiating movement of the associated objects. In other embodiments, specialized equipment measures the focus of the viewer's eyes to determine whether the merged image is perceived by the viewer, automatically initiating separation in response. In any event, a step 214 determines whether the merged image is still perceived by the viewer. Similar to step 212, the determination of step 214 may be done manually or automatically. When step 214 determines that the merged image is still perceived, control passes to a step 216. Step 216 continues separating the two associated images along the horizontal line and loops back to step 214. Thus the method 200 constantly monitors and continues motion while the merged image is perceived.

When the merged image is "lost" by the viewer (i.e., the merged image is no longer perceived), step 214 passes control to a step 218 that stops movement of the two associated images. It should be noted that the viewer will at this point perceive four images. This is because the viewer's left eye provides the viewer a first pair of two-dimensional images representing a first projection of the two associated images onto the back of the viewer's left eye, while the viewer's right eye provides the viewer a second pair of two-dimensional images representing a second, distinct, projection of the two associated images onto the back of the viewer's right eye. Then a step 220 provides the viewer a "score" for the exercise. In some embodiments, the viewer's score is merely an indication of the absolute distance separating the two associated images at the moment the viewer lost the merged image. In other embodiments, the score may be based not only upon the absolute separation distance, but also factors such as the separation speed and the characteristics of the associated images. When the score is provided, the eye exercise method 200 is complete in a step 222.

Figure 4:
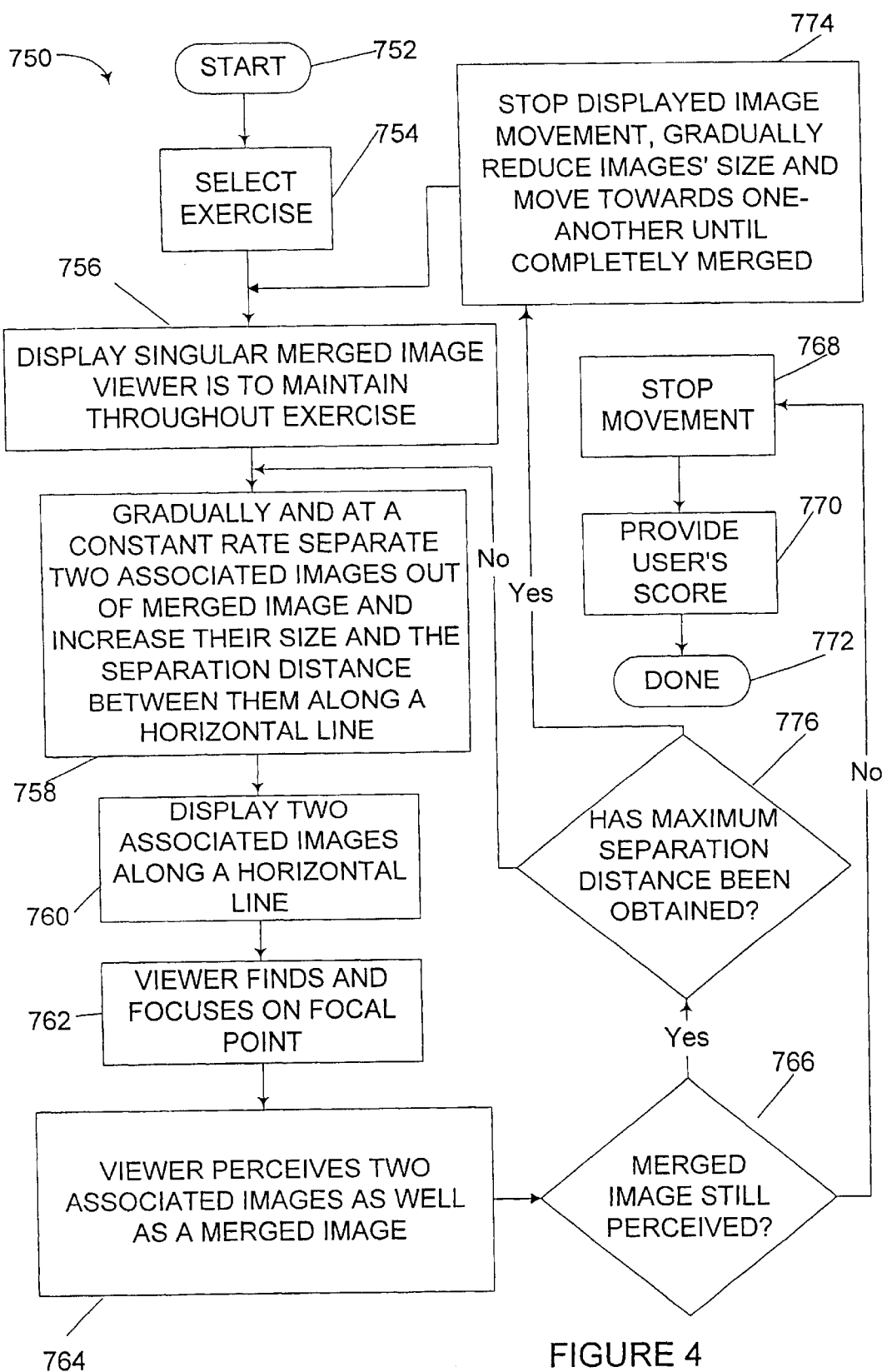
FIG. 4 is a flow chart showing one embodiment of a method in accordance with the present invention by which a viewer may exercise his or her eyes.

FIG. 4 is a flow chart illustrating the eye exercise method 750 in accordance with one preferred embodiment of the present invention. In a start step 752, the exercise method 750 begins. Step 752 includes any initialization process required to prepare for the exercise method 750. For example, if the method 752 is implemented on a computer system, step 752 includes turning on the computer and executing the software that implements the method 752. Then, after initialization, a step 754 selects an appropriate and/or desired exercise. As is described in more detail with reference to FIGS. 5, 6, 7, 10, and 11, some embodiments of the invention permit a viewer to select, or have selected for him, exercises of varying difficulty and character. By way of example, parameters such as selected images' perceived patterns, the associated images separation speed, a starting separation distance between associated images, and an absolute image size are all suitable parameters for the viewer to manipulate. One suitable embodiment for selecting exercises in step 754 is described below in FIG. 10. A suitable embodiment for having exercises selected for the user is described below in FIG. 11. In any event, after step 754, a next step 756 displays a single merged image.

In step 756 a single merged image is displayed at approximately the center of the display screen. The single merged image described in step 756 corresponds to the image the viewer seeks to perceive once, as in step 758, two associated begin to move away from each-other along an axis running essentially horizontal to the user ("the horizontal line"). In step 760 the two associated images have moved far enough apart such that two distinct yet associated images are displayed on the screen. In a step 762 the viewer locates a central focal point of the two associated images. As described above, the central focal point lies between the viewer and the two associated images along a focal line. The focal line is approximately perpendicular to the horizontal line and intersects a point on the horizontal line that is approximately centered between the two associated images.

As the two associated images move away from each-other, two distinct images are displayed along the horizontal axis. The actual location of the central focal point will vary based on the particular viewer and the characteristics of the associated images. By focusing on the focal point, in a step 764, the viewer will perceive a merged image in addition to the two associated images unless the strength of the viewer's eye muscles has deteriorated to such an extent as to prevent the necessary eye coordination required for merging the two displayed images. It will be appreciated that the viewer's ability to perceive the merged image will vary with the particular viewer's visual capabilities as well as his or her current level of eye fatigue and eye strain.

In step 766 the exercise allows the user to signal to the computer that his ability to perceive the merged image has been interrupted or failed at any time during the exercise. Upon receipt of a signal that the viewer's ability to perceive the merged image has failed, step 772 will stop the movement of the displayed images. Step 774 will display the viewer's score. Step 776 will provide an exit menu from which the user can choose to begin the exercise again or exit the exercise program.

Step 766 provides that if the viewer does not utilize the ability to signal the computer in step 770, the displayed images will continue to move apart gradually along the horizontal axis, increasing in size, until they reach a predetermined maximum separation distance. Increasing the displayed images' size as their separation distance increases, serves to create the illusion that the viewer is gaining a more proximate position to the displayed objects. That is, three dimensional perspective provides that as two distinct objects are viewed from a nearer distance, the objects themselves and the distance between them appear larger in size. Step 758 provides for the application of this illusion of perspective.

In step 774, upon reaching a predetermined maximum distance of separation, the displayed objects reverse their direction and begin to move toward each-other along the horizontal axis. Additionally, step 774 provides that the two displayed objects will decrease in absolute size as the separation distance between them gradually decreases. Again, the objects' diminution in size and separation distance serves to create the illusion of perspective. Represented on a two dimensional surface, distinct objects that are placed further away from the viewer will seem to reduce in size and reduce in the distance that separates them. If the viewer does not utilize the signal provided in step 766, the two displayed images will gradually merge into a single image as displayed upon the exercises' commencement, and the exercise will continue from step 756.

With reference to FIGS. 5(a)–5(c), the stereoscopic vision principle will now be described. As mentioned previously, stereoscopic vision is the ability to perceive distance and the three dimensional properties of a viewed object. In order to have stereoscopic vision, a viewer's pair of eyes must be capable of performing the image merging as illustrated in FIGS. 5(a)–5(c). Because the selectable images of the present invention include characteristics which require such capabilities, the present invention utilizes these different capabilities thereby maintaining them.

FIG. 5(a) illustrates how the viewer merges associated two-dimensional images which have no common objects into a single picture. A snail shell image 150 and a snail body image 152 represent two associated two dimensional images which, when superimposed, create a two dimensional snail image 154. In physical space, an actual snail is a three dimensional object. However, the information which a viewer's brain is provided by the viewer's eyes is a pair of two-dimensional images being, essentially, two different projections of the three dimensional physical space. The viewer must be able to merge these projections, e.g., the snail shell image 150 and the snail body image 152, when presented in order to properly perceive physical space, e.g., the snail body image 154.

FIG. 5(b) illustrates how the viewer must merge associated images when there is overlap, or common objects, between such images. Stick FIGS. 160 and 162 each include a matching body. However, stick FIG. 160 alone has a bag image 164, while stick FIG. 162 alone has a hat image 166. However, the single perceived image a viewer properly perceives is a stick FIG. 168, having the bag image 164 and the hat image 166.

FIG. 5(c) illustrates how a viewer properly merges two associated images in order to implement stereoscopic vision. A circular image 180 includes a left-of-center circle 182 shifted to the left of the center of the circular image 180. A circular image 182 includes a right-of-center circle 186 shifted to the right of the center of the circular image 184. When a viewer properly merges the images, a circular image 188 is perceived having two circles 190 and 192. However, circles 190 and 192 are perceived as symmetrical around a single center point but located with in the same plane. That is, the viewer perceives that a one of the circles 190 and 192 is not in the plane of the paper upon which FIG. 5(c) is illustrated.

With successive reference to FIGS. 6(a)–6(d), an example progressively showing the separation of a plurality of images in accordance with one embodiment of the present invention will now be described. As described above with reference to FIG. 3, the present invention teaches displaying two associated images and separating them along a horizontal line. In FIG. 6(a), the two associated images are a circular image 250 and a circular image 252 shown moving apart as indicated by a double arrowhead line 254. The circular image 250 includes a left-of-center circle 251 shifted to the left of the center of the circular image 250. The circular image 252 includes a right-of-center circle 253 shifted to the right of the center of the circular image 252. When a viewer properly merges the images, a merged circular image 256 is perceived having a dead center circle 257. A first complete view 258 illustrates how the viewer perceives the circular images 250 and 252 along with the merged circular image 256.

FIGS. 6(b) and 6(c) each illustrate the viewer's perception during separation of the associated images 250 and 252 while the merged circular image 256 is still perceived. In FIG. 6(b), an arrowhead line 260 indicates the direction of motion as well as the separation distance between the associated images 250 and 252. A second complete image 262 illustrates how the viewer perceives the circular images 250 and 252 along with the merged circular image 256. Likewise, in FIG. 6(c), an arrowhead line 264 indicates the direction of motion as well as the separation distance between the associated images 250 and 252. A third complete image 266 illustrates how the viewer perceives the circular images 250 and 252 along with the merged circular image 256.

FIG. 6(d) illustrates the viewer's perception once the associated images 250 and 252 have separated such that the merged circular image 256 is no longer perceived. An arrowhead line 268 indicates the direction of motion as well as the separation distance between the associated images 250 and 252. A fourth complete image 270 illustrates how the viewer perceives the circular images 250 and 252 but no longer perceives the merged circular image 256.

In some embodiments of the present invention, viewers will be able to select from a set of images defining differing relative degrees of perceptual difficulty in order to train their eyes at a desired level of difficulty, as well as further enabling viewers to track their progress. FIGS. 7(a)–7(b) illustrate a set of associated image pairs, each member pair inducing the perception of a perceived image 400 having objects 402, 404, 406, 408, and 410. However, because of the differences in common objects between members of the set of associated image pairs, each pair has a different level of exercise difficulty.

FIG. 7(a) shows associated images 420 and 422 each having objects 402, 404, and 406 in common. The associated image pair 420 and 422 of FIG. 7(a) provides the viewer the easiest combination to merge into the perceived image 400 from the image pairs of FIGS. 7(a)–7(d). FIG. 7(b) shows associated images 424 and 426 each having objects 402 and 404 in common. The associated image pair 424 and 426 of FIG. 7(b) is the second easiest of FIGS. 7(a)–7(d). FIG. 7(c) shows associated images 428 and 430 having only object 402 in common. The associated image pair 428 and 430 of FIG. 7(c) is the third easiest of FIGS. 7(a)–7(d). FIG. 7(d) shows associated images 432 and 434 having no objects in common. Of FIGS. 7(a)–7(d), the associated image pair 432 and 434 of FIG. 7(d) is the hardest combination for the viewer to merge. By selecting from a set such as shown in FIGS. 7(a)–7(d), the viewer can determine the desired level of difficulty.

With successive reference to FIGS. 8(a)–8(i), an example progressively shows a singular merged image gradually separating into a plurality of images whose absolute size and separation distance gradually increase until a maximum separation distance is obtained. Once maximum separation distance is obtained, the objects begin to move back towards each-other simultaneously reducing in absolute size and in separation distance. As described above with reference to FIG. 4, the present invention teaches displaying one merged image, which separates into two associated images that gradually separate along a horizontal line. In FIG. 8(a), the single merged image consists of a circular image 831 including an external circular shape 832 and an internal circular shape 834. Note that the right-most portion of FIG. 8(a) consists of a complete view 891 representing the viewer's perspective of the displayed images according the embodiment of the present invention.

In FIG. 8(b) the single merged image has begun to separate into a pair of associated images, each consisting of a outer and inner circular image. The image moving to the viewer's left consists of outer circular image 836 and an inner circular image of 838. The image moving to the viewer's right consists of an outer circular image 840 and inner circular image 842. At this stage in the exercise the viewer continues to perceive just the displayed images. Thus, the illustration pertaining to the viewer's perceptual experience, the "complete view" 893, appears similar to the displayed images.

In FIG. 8(c) the two associated objects have moved a sufficient distance apart along horizontal line 892 as to be displayed as distinct images. Arrowhead line 892 indicates the direction of motion as well as the separation distance between associated images 836 and 840. Notice in complete view 895 that a central image 875 appears. Image 875 consists of external circular image 876 and inner circular image 878. This image appears to the viewer but is not an image displayed on the computer screen. Also apparent in FIG. 8(c) is the aspect of the displayed images concerning the relative location of the inner circular images, here 846 and 850 respectively. Unlike the inner circular image 878 of the perceived central image 875, inner circular image 846 is positioned to the right of center relative to outer circular image 844. Inner circular image 850 is positioned left of center relative to outer circular image 848. In addition to the feature of the complete view that an additional image 875 appears, note that the relative position of inner circular image 878 is central to outer circular image 876.

Likewise, in FIG. 8(d), an arrowhead line 894 indicates the direction of motion as well as the separation distance between the associated images 860 and 864. A third complete view 897 illustrates how the viewer perceives the merged circular image 877 in addition to the displayed circular images 860, 862, 864, and 866.

FIG. 8(e) illustrates the displayed images 868, 870, 872 and 874 at a maximum size and separation distance. Notice that horizontal line does not contain arrowheads indicating movement of the objects. Movement of the objects has terminated due to maximum separation distance or the viewer's loss of the focal point. Complete view 899 illustrates the potential loss of focal point and loss of merged image that may occur at any time during the exercise. Merged image 879 is shown as a lighter tone to indicate the viewer's potential inability to perceive the merged image. If the viewer does in fact lose his focal point and can no longer perceive the merged image, the merged image will be entirely absent from the viewer's field of view.

FIGS. 8(f)–8(i) illustrate the continuation of the exercise and the gradual decrease in object size and separation distance as the displayed objects begin to move towards one-another and eventually merge. Horizontal lines 881 and 883 again bear arrowheads indicating the displayed objects' direction of movement. Once the objects merge entirely, as illustrated in step 8(i), the eye exercise re-commences and the objects begin to separate once again.

In some embodiments of the present invention, viewers will be able to select or have selected for them, a set of images defining different degrees of perceptual difficulty. Various levels of difficulty are utilized in order to train viewer's eyes at a desired level of difficulty and to enable viewers to track their progress. FIGS. 9(a)–9(i) illustrate the stages of an exercise in which a more complex pair of associated images are used. That is, the associated images illustrated in FIGS. 9(a)–9(i) are more difficult for a viewer to merge than the associated images illustrated in FIGS. 8(a)–8(i). FIGS. 9(a)–9(i) successively illustrate a single merged image gradually separating into a plurality of images whose size and separation distance gradually increase until a maximum separation distance is obtained. Once a maximum separation distance is obtained, the objects begin to move back toward one-another and reduce in size until they obtain a merged position similar to that position held at the commencement of the exercise.

The set of associated pairs displayed as distinct objects in FIGS. 9(b)–9(h) consist of a circular image encasing a 'Z'-like object and a smaller circular image positioned behind the diagonal of the 'Z'. These images are illustrated in FIG. 9(c) as circular object 920, backwards 'Z'-like object 924, and small circular object 922 positioned behind the diagonal of 924. The associated image illustrated in FIG. 9(c) consists of circular object 926, encased 'Z'-like object 930, and small circular object 928 positioned behind the diagonal of the 'Z'. A viewer of sufficient capacity can find a focal point which provides the appearance of merged object 967, illustrated in complete view 995. Like merged image 901, merged image 967 appears as an hour glass design 966 with two small circular shapes 962 and 964 positioned beside the central crossing point of the hour glass, all encased within a circle 968.

FIGS. 9(*d*)–9(*e*) illustrate the continued gradual increase in displayed image size and separation distance, while illustrating the viewer's perception up until maximum separation and potential loss of focal point and failure to perceive the merged image. The potential loss of focal point and inability to perceive the merged image is illustrated in FIG. 9(*e*) by lightly colored central object 911 shown in complete view 999. In the illustration of the displayed images, notice that horizontal line 954 does not contain arrowheads indicating movement, but instead illustrates that the movement of the objects has momentarily ceased at maximum separation distance or the viewer's loss of the focal point. FIGS. 9(*f*)–9(*i*) illustrate the gradual decrease in size and separation distance of displayed objects until eventual merging and re-commencement of the eye exercise at FIG. 9(*i*). Arrowhead lines 941 and 943 illustrate the direction as which the objects are moving and the gradually decreasing separation distance between the displayed objects. FIGS. 9(*f*)–9(*i*) likewise illustrate the corresponding complete view, representing the viewer's perspective upon successful maintenance of the viewer's focal point. If the viewer is able, a third merged image will be perceived until the associated images become too near to one-another as illustrated in FIG. 8(*h*). Upon complete merger of the displayed images illustrated in FIG. 9(*i*), the eye exercise re-commences and the displayed images began to move apart as illustrated in FIG. 9(*b*).

Figure 10:
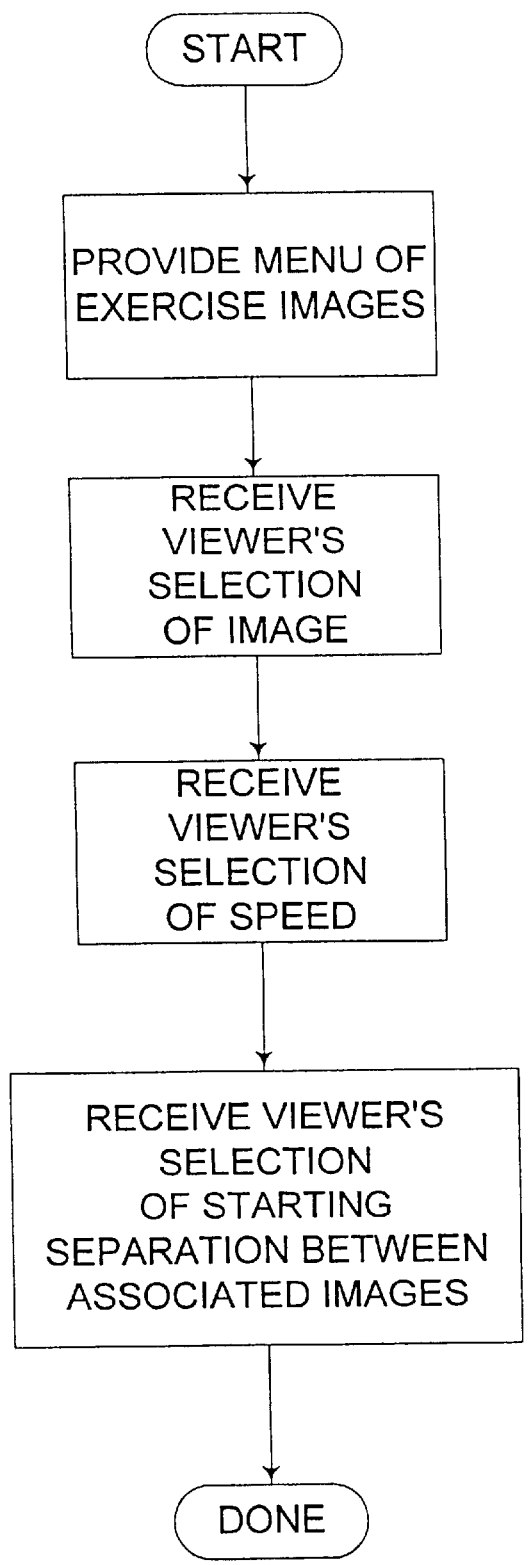
FIG. 10 is a flow chart showing one method of selecting the desired exercise in accordance with yet another aspect of the present invention.

Turning next to FIG. 10, one suitable embodiment of exercise selection step 204 of FIG. 3 will now be described. The embodiment of FIG. 10 is well suited for use on a pointer driven computer system, but is suitable in other applications such as a television implementation. The steps of FIG. 10 allow viewers to customize an eye exercise for their particular needs, based upon current eye strain and fatigue, mood, and individual ability.

Any necessary initializing is performed in a step 298. The relevant substantive functionality of FIG. 10 begins with a step 300 providing a menu of selectable exercise images. As described above, the characteristics of the associated images effects the level of difficulty of the exercise. Thus a viewer may select a particular exercise image based upon personal preferences including visual appearance and desired level of difficulty. A step 302 receives the viewer's selection of an exercise image according to some suitable mechanism. For example, the viewer may scroll through the menu, position the pointer over the desired exercise image, and "double click" on the desired exercise image. A next step 304 receives the viewer's selection of separation speed according to some suitable mechanism. Suitable mechanisms include a data entry field enabling the viewer to enter a specific speed, a menu providing specific speeds, or a menu providing a set of relative separation speeds (e.g., "slow," "medium," and "fast"). Again, the faster the separation speed, the more difficult the exercise. Another step 306 receives the viewer's selection of starting separation between the associated images. Similar to step 304, the distance may be entered via a data entry field or some menu driven mechanism.

Since the temporal ordering of steps 300–306 is not particularly relevant to the present invention, steps 300–306 may be performed in any order. In addition, it is contemplated that the present invention will have a variety of embodiments having differing combinations of these steps. For example, some embodiments will only allow the viewer to select a desired image, the separation speed and starting separation distance being predefined. In other embodiments, the user might simply select a desired level of difficulty, the method determining the image, speed, and starting separation distance based upon the selected level. In addition, it is contemplated that other embodiments will enable viewers to manipulate a plethora of additional parameters including size of images, coloring of images, and even allow viewers to introduce their own images for use in performing exercises.

Figure 11:
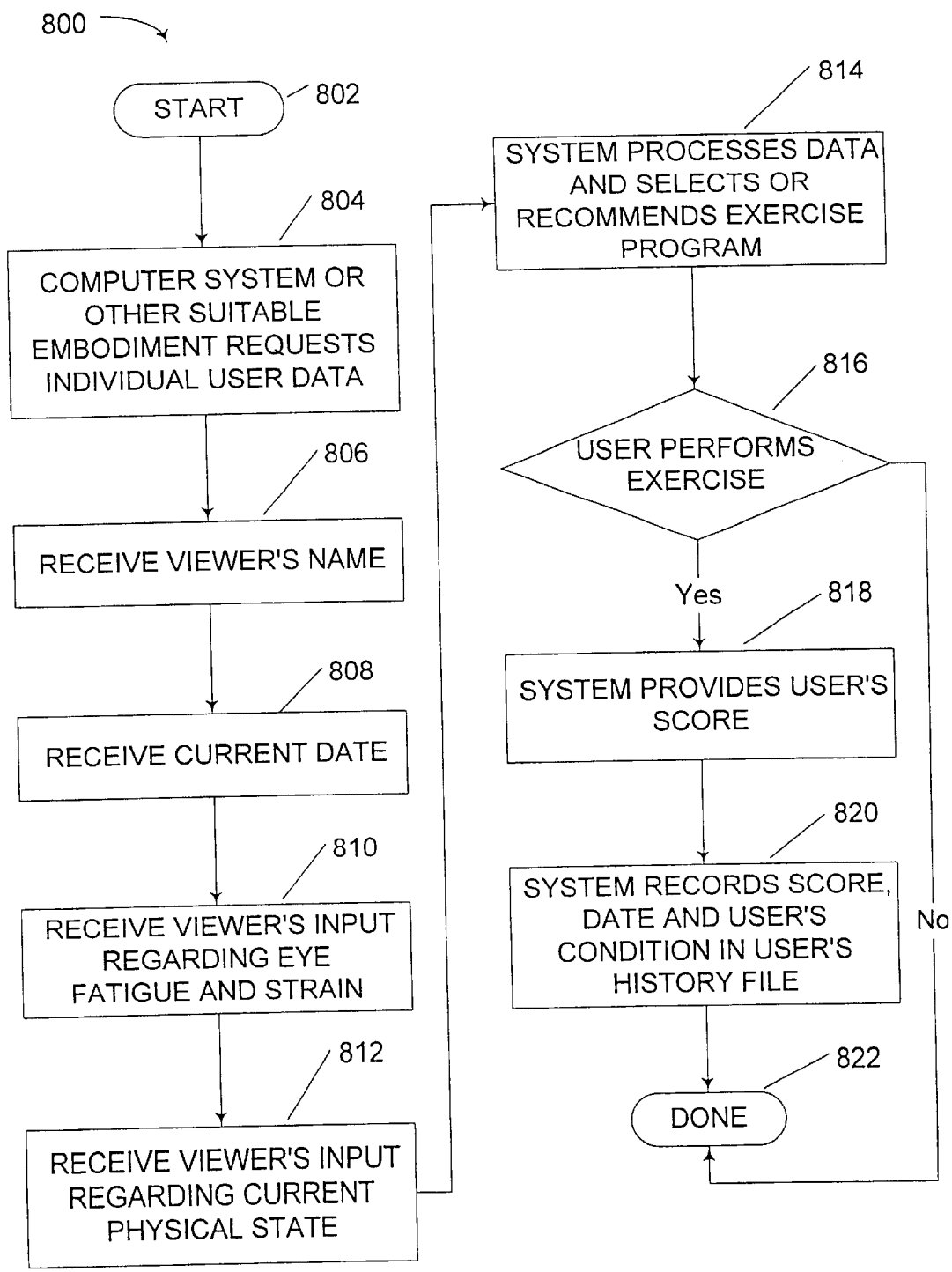
FIG. 11 is a flow chart showing one embodiment of a method in accordance with the present invention by which a viewer may exercise his or her eyes.

FIG. 11 is a flow chart illustrating an eye exercise method 800 in accordance with one aspect of the present invention. Method 800 embodies an aspect of the present invention wherein the user is able to select or recommend an eye exercise program based on various data input by the user. The embodiment of FIG. 11 is well suited for use on a pointer driven computer system, but is suitable in other applications in accordance with such as a television implementation. In a start step 802, the exercise method 800 begins. Step 802 includes any initialization process required to prepare for the exercise method 800.

The relevant substantive functionality of FIG. 11 begins with a step 804 requesting individual user data. In step 806 the exercise receives the user's name. In step 808 the exercise receives the current date. In step 810 the exercise receives various data relevant to the user's current degree of eye strain and fatigue. In step 812, the exercise receives data regarding the user's general physical state, especially the user's general level of fatigue. Since the temporal ordering of steps 806-812 is not particularly relevant to the present invention, steps 806–812 may be performed in any order. Additionally, it is contemplated that the present invention will have a variety of embodiments having differing combinations of these steps, and of these steps in conjunction with steps 302-306, referred to above and shown in FIG. 6. That is, in some embodiments, the viewer may not only be able to provide all or some of the data by which the system can recommend an exercise and update the user's person history file, but the viewer may also be able to select or manipulate various parameters of the exercise to be performed.

In step 814 the exercise system processes the data received and selects for or recommends to the user an eye exercise program. In step 816 the user is given the option of performing the exercise, illustrated above in FIG. 4, or the user may terminate the program. Termination of the program is shown in step 822. If the user performs the exercise, step 818 provides the user's score upon termination of the exercise. In step 820, the user's score and the data inputted at steps 806–812 are recorded in the user's individual history file. If the user decides not to perform another exercise, the program ends in step 822.

Figure 12:
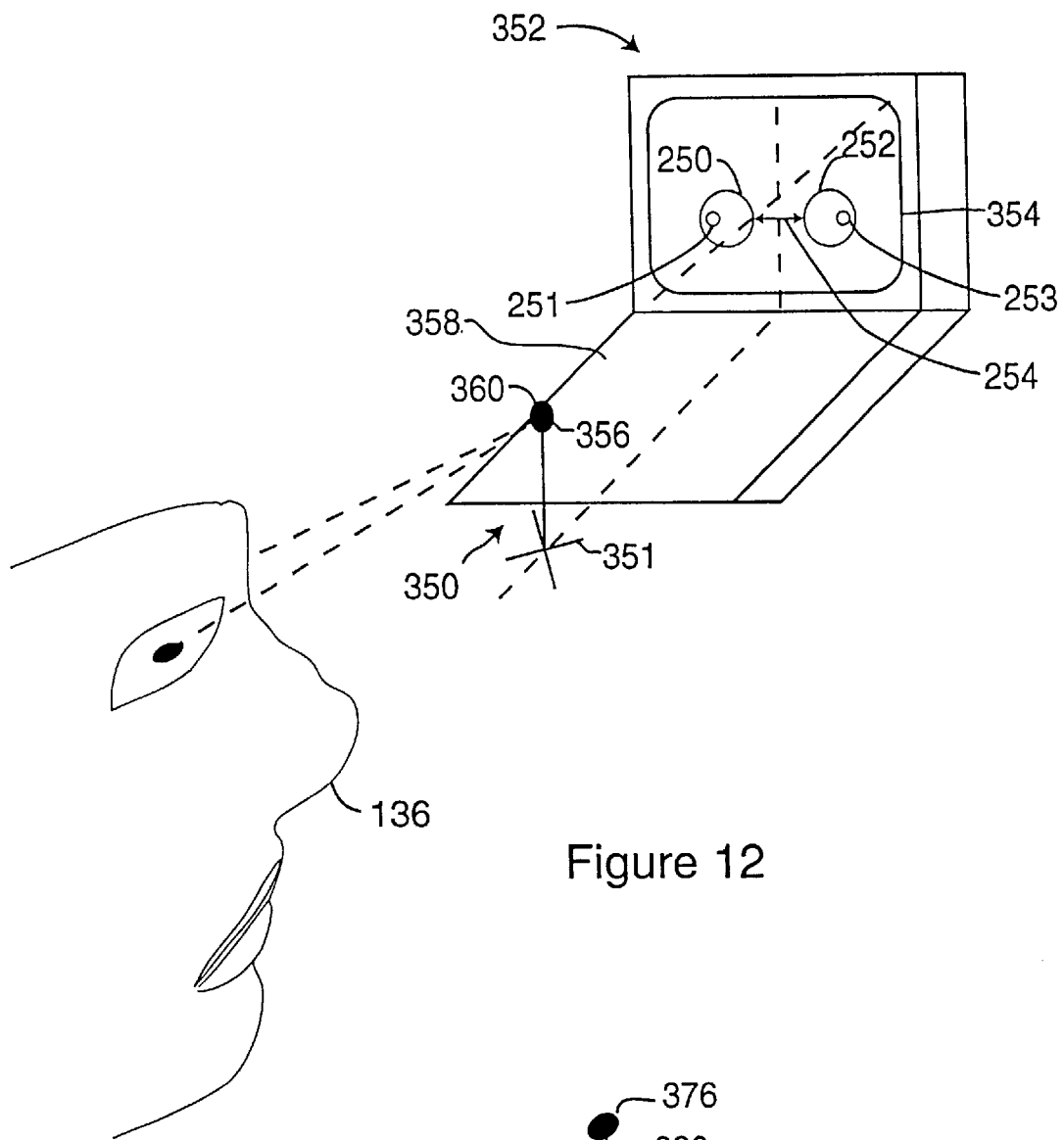
FIG. 12 is a pictorial illustration showing a free-standing apparatus for finding the central focal point in accordance with still another aspect of the present invention.

With reference to FIG. 12, one embodiment of an apparatus 352 in accordance with the present invention, for aiding a viewer 136 in relieving eye strain and/or eye fatigue, will now be described. FIG. 12 illustrates a viewer 136 gazing towards a display system 352 including a display screen 354 and a free-standing apparatus 350, the free standing apparatus 350 having a base 351 and a tip 360 that defines a central focal point 356. The display screen 354 is displaying two associated images: a circular image 250 and a circular image 252 shown separating as indicated by an arrowhead line 254. The circular image 250 includes a left-of-center circle 251 shifted to the left of the center of the circular image 250. The circular image 252 includes a right-of-center circle 253 shifted to the right of the center of the circular image 252. As described above with reference to FIG. 6(a), when the viewer 136 properly merges the images by focusing on the central focal point 356, a merged circular image 256 is perceived having a dead center circle 257. As further described above with reference to FIG. 6(a), a first complete view 258 illustrates how the viewer 136 perceives the circular images 250 and 252 along with the merged circular image 254.

In order to perceive the merged circular image, the viewer 136 must locate the central focal point 356 of the two associated images, the central focal point 356 lying along a focal line 358 between the viewer and the two associated images. The focal line 358 is perpendicular to the horizontal line along which the associated images move and intersects a point on the horizontal line that is centered between the two associated images. As shown in FIG. 7, the apparatus 350 has been positioned such that its tip 360 overlaps the central focal point 356. Thus the viewer 136 can focus on the tip 360, thereby focusing on the central focal point 356.

Figure 12A:
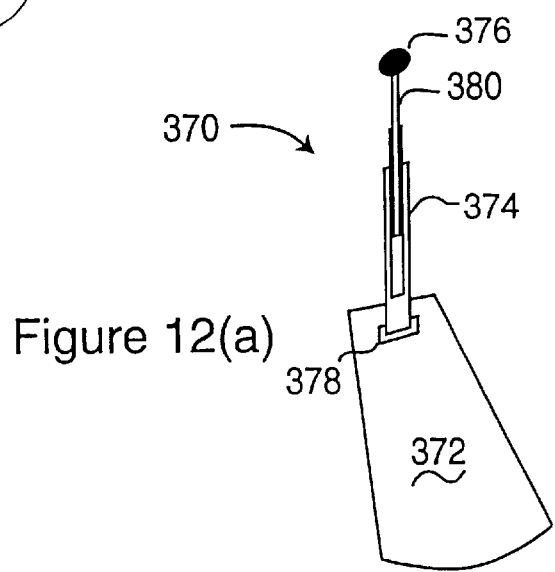
FIG. 12(a) is a pictorial illustration showing a free-standing apparatus in accordance with a separate embodiment of the present invention.

Turning next to FIG. 12(a), a further embodiment of a free standing apparatus 370 in accordance with the present invention will now be described. The free standing apparatus 370 includes a base 372, a telescopic stem 374, and a focal tip 376. The telescopic stem 374 has a number of sections, such as a most distal section 380, that slide one inside of another allowing the telescopic stem 374 to extend and contract. The telescopic stem 374 is attached to the base 372 by way of a hinge 378 enabling the telescopic stem 374 and the base 372 to fold together. The tip 376 is located at a distal end of the telescopic stem 374 with respect to the base 372. In general, the tip 376 is of a larger circumference than the most distal section 380. The free standing apparatus 370 may be easily adjusted in order to aid a viewer in finding and focusing on a central focus point such as central focus point 356 of FIG. 12.

The free-standing apparatus 350 may take many suitable forms. For instance, in some embodiments the top 360 will be detractable and the stand 351 foldable such that the free-standing apparatus 350 may be compacted to a decreased shape. In one embodiment, described below with reference to FIGS. 12(b) and 12(c), the free-standing apparatus is configured as an ocular device combined with a computer input device, such as a mouse. Such a configuration will be appreciated as allowing a computer user to access the free-standing device with minimal effort or clutter of the user's workspace. In additional embodiments, the ocular device is incorporated into a variety of computer input devices such as a keyboard or a trackball.

Figure 12B:
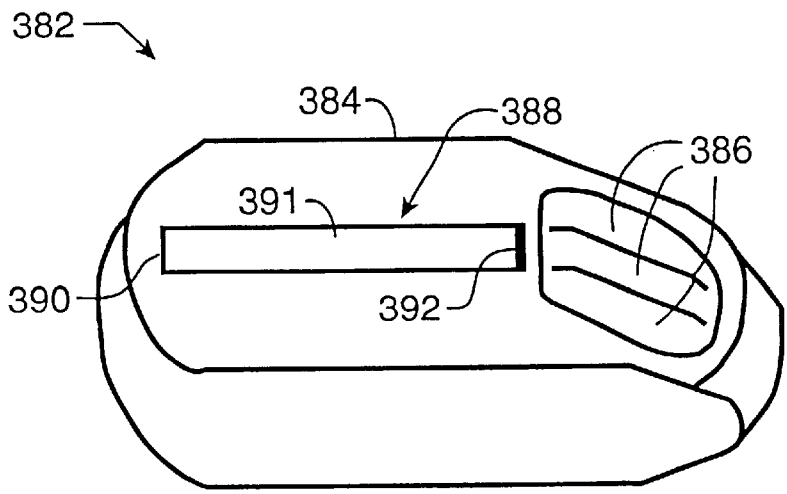
FIG. 12(b) is a pictorial illustration showing a mouse pointing device having an ocular device in accordance with yet another embodiment of the present invention.
Figure 12C:
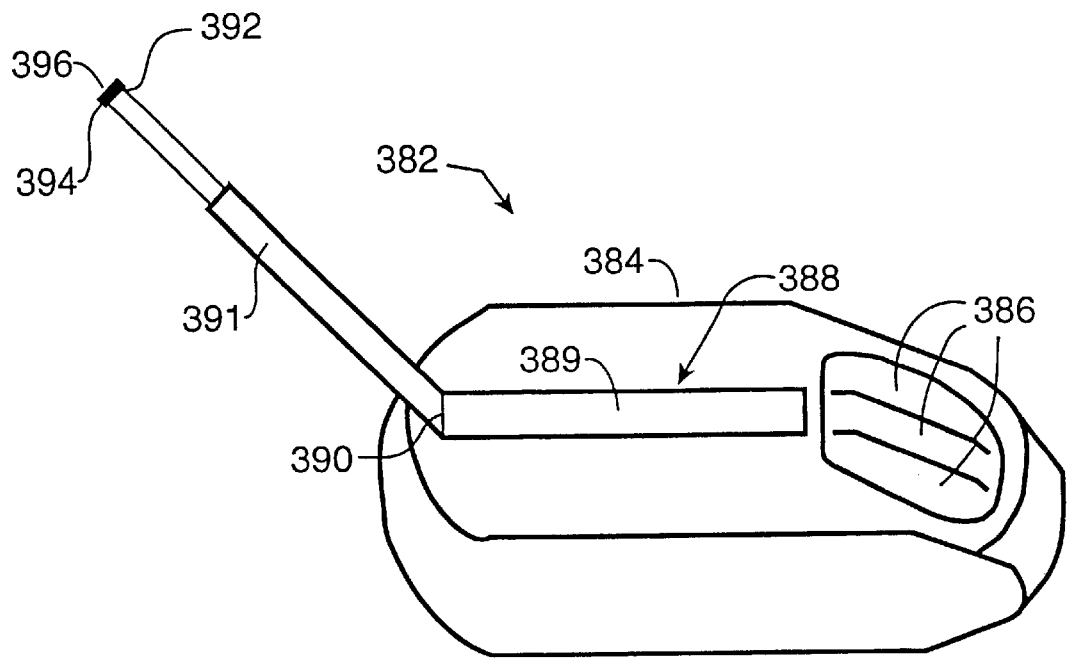
FIG. 12(c) is a pictorial illustration of the mouse pointing device of FIG. 12(b) wherein the ocular device has been unfolded and extended.

With reference to FIGS. 12(b) and 12(c), a mouse pointing device 382 in accordance with one embodiment of the present invention will now be described. The mouse pointing device 382 includes a housing 384, buttons 386, an ocular device 388, a receiving slot 389, and a hinge 390. The housing 384 typically bears a resemblance to a mouse; hence the fanciful name. When the mouse pointing device is an electromechanical device, typically electronics and a rollerball are built into the housing 384 and are arranged to provide position data for controlling a cursor positioned upon a computer screen. Other suitable mouse pointing devices, such as digitizers, are purely electrical and thus do not require a trackball. The buttons 386 allow a user to enter other data besides positional data into a computer system coupled thereto. The design of mouse pointing devices and digitizers, and their interface with computer systems, is well known to those skilled in the art.

The ocular device 388 of FIGS. 12(b) and 12(c) includes a telescopic stem 391, a focal tip 392, a position sensor 394, and a push button 396. The telescopic stem 391 has a number of sections that slide one inside of another allowing the telescopic stem 391 to extend and contract. The telescopic stem 391 is attached to the housing 384 by way of a hinge 390 enabling the telescopic stem 391 and the housing 384 to fold together. In the embodiment of FIGS. 12(b) and 12(c), when the telescopic stem 391 is fully contracted and the ocular device folded into the housing 384, the receiving slot 389 flushly receives the ocular device 388. A viewer may use the ocular device 388 in conjunction with the computer controlled exercises described elsewhere in the present application to perform exercises for relieving eyestrain. Alternatively, the viewer may use the ocular device to perform standard convergence exercises with his or her eyes. Thus by incorporating the ocular device into a device frequently present in the typical workspace, the present invention provides a convenient, space efficient mechanism for performing eye exercises.

The position sensor 394 is shown located upon the focal tip 394, which is a preferred location. The position sensor 394 is operable to measure a distance from the mouse pointing device 382 to a viewer using the ocular device 388 for eye exercises. This distance information may be transmitted to the computer system and used for implementing the eye exercises. The push button 396 is positioned upon the focal tip 394. In preferred embodiments, engagement of the push button 396 causes data related to the eye exercise software to be transmitted to the computer system. For example, pushing the button 396 may simply initiate the execution of the eye exercise software. In preferred embodiments, any additional electronics necessary for implementing the position sensor 394 and/or the button 396 are located within the housing 384.

As will be appreciated, the housing 384 of a conventional mouse input device often has vacant space available therein. Thus any additional electronics or mechanical devices required by the present invention may simply be included within the space already available in a conventional mouse input device. However the housing 384 of the mouse input device 382 may be designed larger as necessary.

Figure 13:
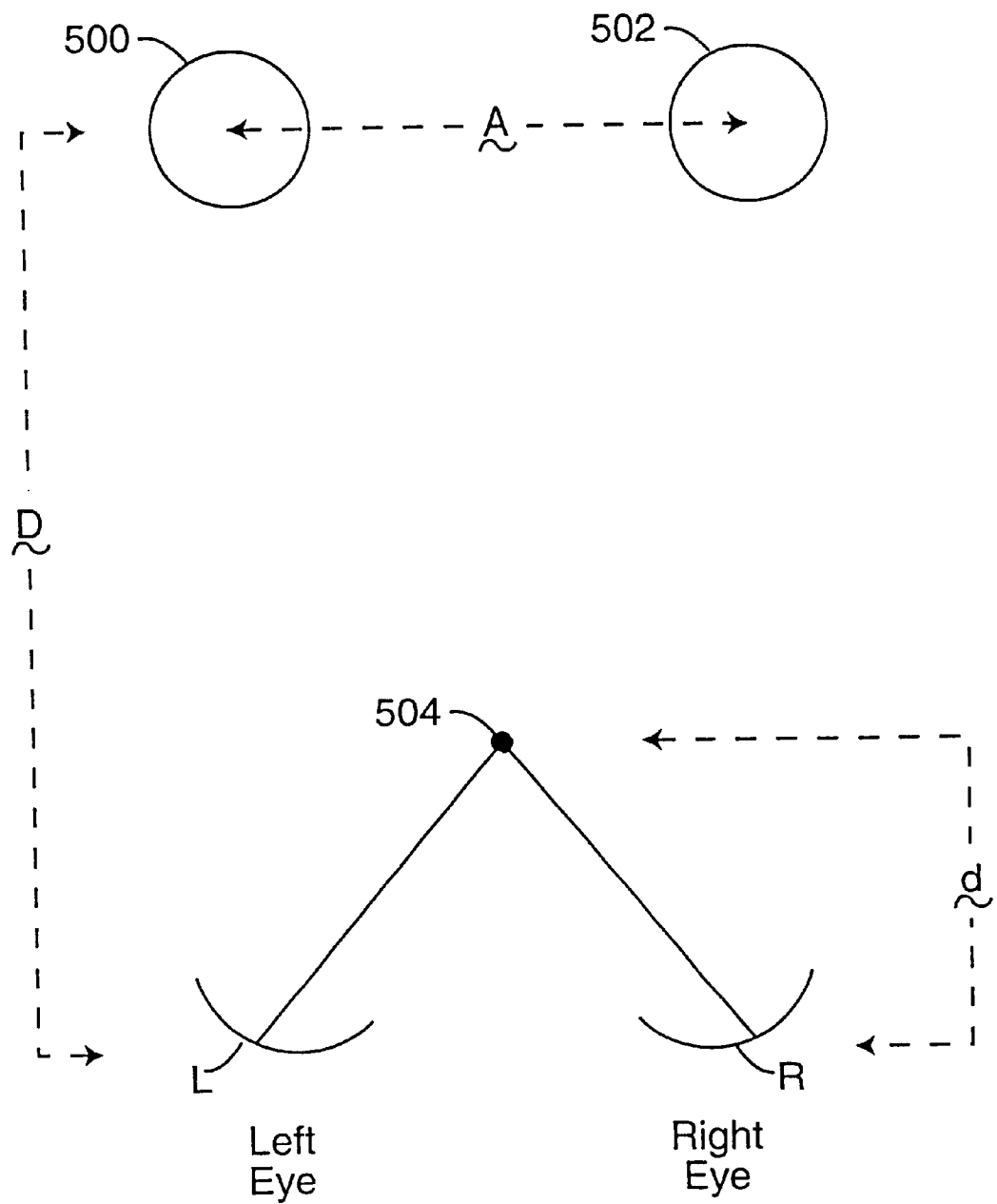
FIG. 13 is a diagrammatic illustration of the spatial relationships among the distances between a viewer's eyes and a central focal point (d), the viewer's eyes and images being projected (D), and the distance between the projected images (A)

With reference to FIG. 13, the parameters defining the relationship between a viewers left and right eyes L and R, two associated circular images 500 and 502, and a central focal point 504 will now be described. The circular images 500 and 502 are separated by a distance "A." The left and right eyes L and R are located at a first distance "D" away from the circular images 500 and 502 and at a second distance "d" away from the central focal point 504. The following relationships among A, D, and d have been determined by experimentation and are expected to provide a reasonably accurate guide for a viewer attempting to focus upon the central focal point 504.

An increase in the distance A with distance D held constant requires the viewer to decrease the distance d, i.e., draw the central focal point closer. A decrease in the distance A with distance D held constant requires the viewer to increase the distance d. Thus distances A and d are approximately inversely proportional.

An increase in distance D with distance A held constant requires the viewer to increase the distance d. A decrease in distance D with distance A held constant requires the viewer to decrease the distance d. Thus distances D and d are approximately directly proportional.

In one example illustrating the above-described relationships, the following measurements were obtained for an individual viewer. To obtain a satisfactory focus on the central focal point 504 when the distance d was approximately 5 inches and the distance A was approximately 3 inches, the viewer had to be positioned such that the distance D was approximately 12 inches. Adjusting the distance A between the images to approximately 4 inches, the viewer had to move away from the associated images such that the distance D was approximately 15 inches, or, alternatively, move the central focal point 504 closer such that the distance d was approximately 3.5 inches. As will be appreciated, these figures may vary somewhat from person to person due, at least in part, to physical factors such as the individual's separation between eyes, as well as the physical characteristics of the eyes.

Although only a few embodiments of the present invention have been described, it should be understood that the present invention may be embodied in many other specific forms without departing from the spirit or scope of the invention.

The methods of the present invention may be implemented in a variety of ways upon a computer system. A representative computer 600 suitable for use in implementing the present invention is illustrated schematically in FIG. 14. Computer 600 includes a central processing unit (CPU) 602 which is coupled bidirectionally with random access memory (RAM) 604 and unidirectionally with read only memory (ROM) 606. Typically, RAM 604 is used as a "scratch pad" memory and includes programming instructions and data for processes currently operating on CPU 602. ROM 606 typically includes basic operating instructions, data and objects used by the computer to perform its functions. In addition, a mass storage device 608, such as a hard disk, CD ROM, magneto-optical (floptical) drive, tape drive or the like, is coupled bidirectionally with CPU 602. Mass storage device 608 is a computer readable medium and generally includes additional programming instructions, data and objects that typically are not in active use by the CPU, although the address space may be accessed by the CPU, e.g., for virtual memory or the like. The computer 600 typically includes input media such as a pointer device 610 keyboards (e.g., a mouse or stylus), and a network interface 614. Additional mass storage devices (not shown) may also be connected to CPU 602 through the network interface 614. The computer 600 further includes a display screen 616. It will be appreciated by those skilled in the art that the above described hardware and software elements, as well as the networking devices, are of standard design and construction, and will be well familiar to those skilled in the art.

Figure 15:
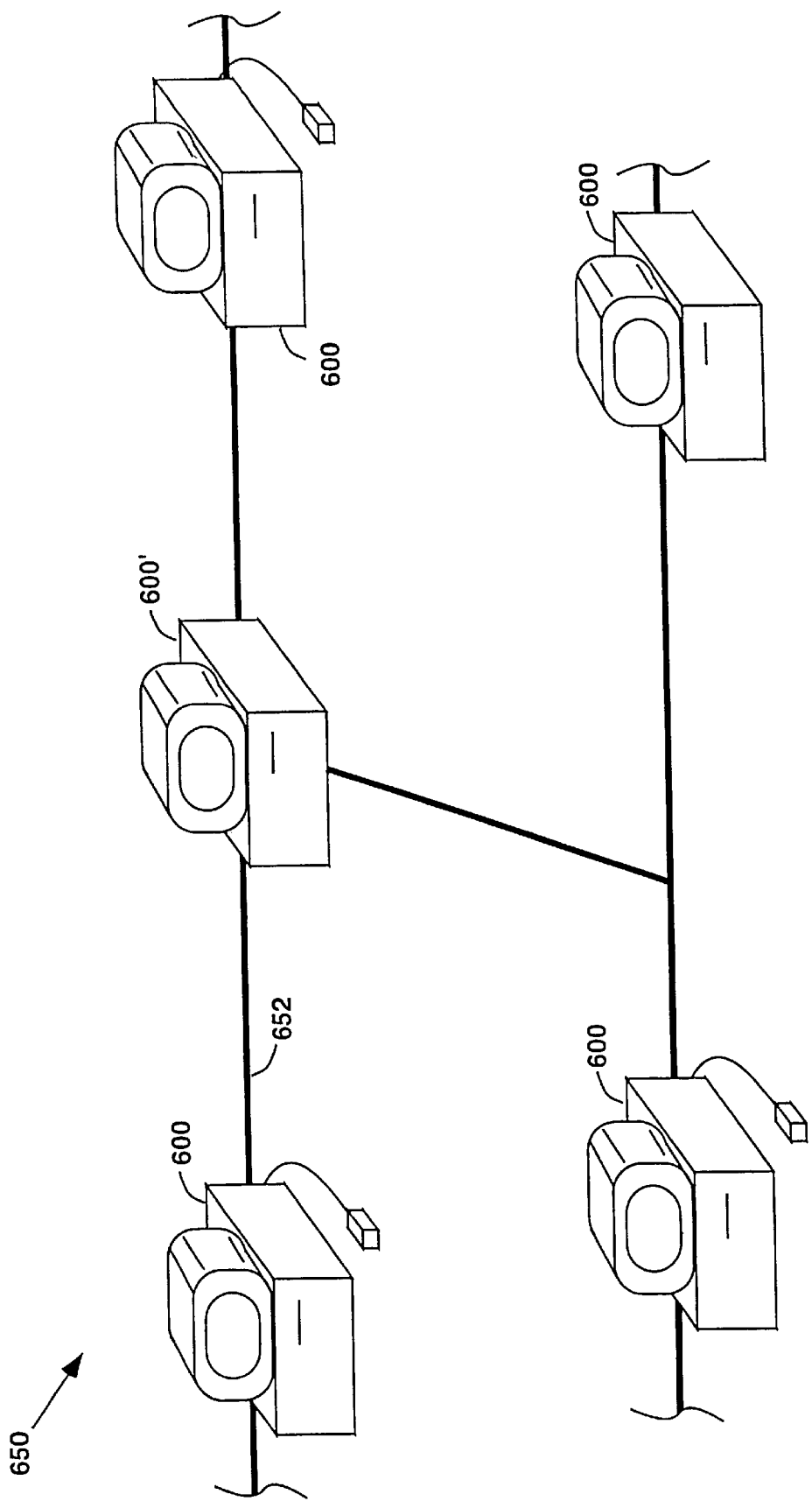
FIG. 15 is a pictorial illustration of various computers linked together in a computer network.

In some embodiments of the present invention, a plurality of computers such as computer 600 are coupled together over a network. The network may take any suitable form. By way of example, a representative network arrangement 650 is illustrated in FIG. 15. The network arrangement 650 includes a first computer 600 which is coupled to a transmission line 652. The network 650 further includes a server, router or the like 600' in addition to other computers 600 such that data and instructions can be passed among the networked computers. The network 650 may be simply a local network or may correspond to a global network such as the Internet. The design, construction and implementation of computer networks will be familiar to those of skill in the art.

Figure 14:
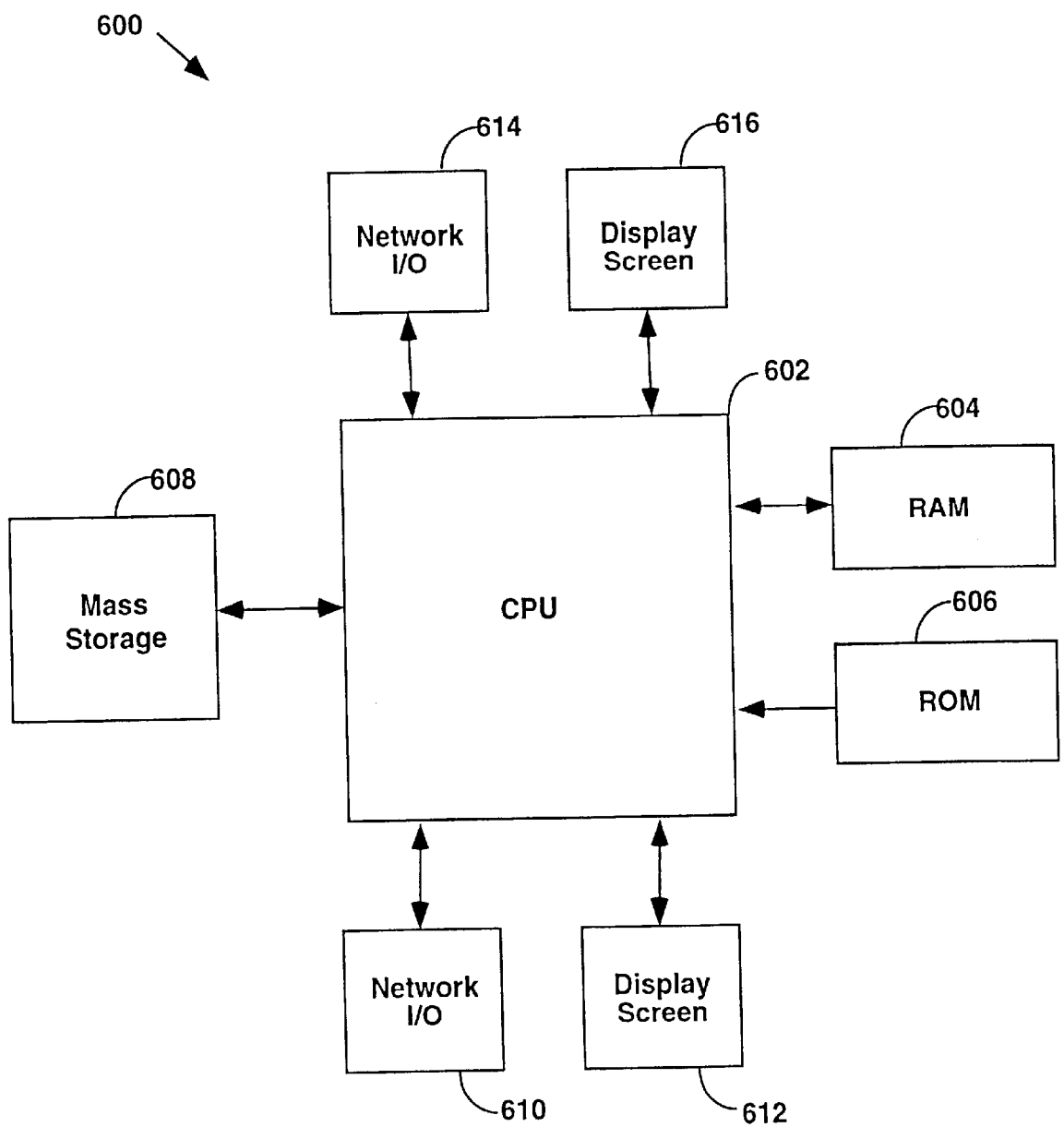
FIG. 14 is a diagrammatic illustration of the major components of a computer in accordance with one embodiment of the present invention.

In a first computer system embodiment of the present invention, a method such as method 200 of FIG. 3 may be implemented as separate software executable upon a personal computer system such as the computer 600 of FIG. 14. As independent software, the computer user must separately initiate a process executing the software in order to facilitate its operation. However, once initiated, the user may immediately perform the exercises and/or place the process in the background. In a related embodiment, the process would then, without substantively effecting other application(s) currently executing, monitor the computer system's use, and, based upon the duration of computer use, prompt the user to perform one or more of the above-described exercises.

In a second computer system embodiment, the methods of the present invention may be integral to a computer operating system. Thus, it would be unnecessary for the user to independently initiate a process executing such methods. However, it is contemplated that the user would still maintain control over the operation, being able to adjust the available parameters including the timing of the prompts, etc.

In still a third computer system embodiment, the methods of the present invention may be integrated into a device driver for the computer system's display monitor. Again, it would thus be unnecessary for the user to independently initiate a process executing such methods. However, it is contemplated that the user would still maintain control over the operation, being able to adjust the available parameters including the timing of the prompts, etc.

Figure 16:
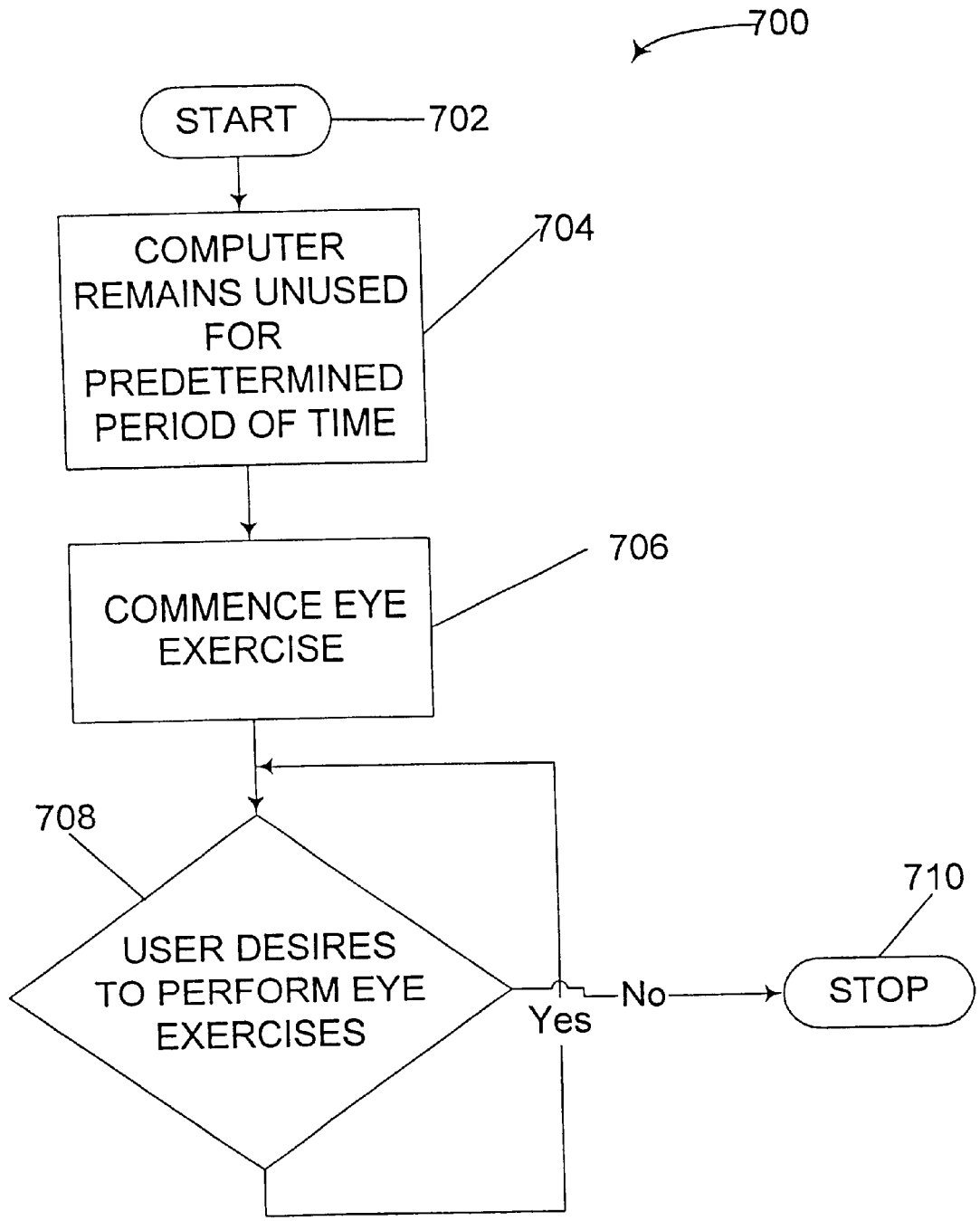
FIG. 16 is a flow chart showing one embodiment of a method in accordance with the present invention by which a viewer may exercise his or her eyes.

According to a fourth computer system embodiment, the methods of the present invention are implemented via a screen saver running on the computer system 600. This embodiment is best illustrated in FIG. 16. At FIG. 16 there is shown a flow chart illustrating an eye exercise method 700 in accordance with one aspect of the present invention. In a start step 702, the exercise method 700 begins. Step 702 includes any initialization processes required to prepare for the exercise method 700. In this particular embodiment of the present invention, method 700 is implemented on a computer system, such that step 702 includes turning on the computer and executing the software that implements the computer's screensaver. As will be appreciated, a screen saver prevents phosphorescence burn in on the display screen of an image displayed upon the display screen for a long period of time. In this embodiment, circumstances such as non-use of the powered computer for a pre-defined period of time would invoke the screen saver of the present invention. Generally, the screen saver would then either blank the screen, present a demonstration of the methods of the present invention, display a company logo, or generate some sort of screen saving display.

In accordance with the present embodiment, step 702 includes designation of the present invention as the computer system's screensaver. Thus, step 704 includes computer non-use for a pre-determined period of time, triggering the utilization of the established screen saver, this embodiment of the present invention having been chosen at initialization step 702. After a predetermined period of computer non-use has transpired 704, the eye exercise commences in step 706. The user may perform the eye exercise for as long as he or she chooses. One suitable embodiment of the eye exercise is described below with reference to FIG. 4. In any event, when the user no longer desires to perform the eye exercise, in step 710 the user recommences interfacing with the computer. It will be appreciated that a common means for terminating the screen saver mode is by the user's attempt to interface with the computer.

In accordance with another embodiment of the present invention, the eye exercise will not be executed upon a predetermined time of powered computer non-use as the computer's screen saver. Instead, upon the user's return to the powered computer and a renewed attempt to interface with the computer, the screen saver will terminate and the initialization step of the eye exercise will cause to be displayed a query regarding the user's desire to perform an eye exercise. If the user responds positively, the eye exercise will commence and continue until the user signals for the exercise's termination. If the user responds to the initial query in the negative, the query will exit and the process in place before execution of the screen save will resume.

In a fifth computer system embodiment, the methods of the present invention may be remotely accessible over a wide area network such as the Internet. For example, the methods of the present invention may be available to paid subscribers of a Web site, the user accessing them by connecting a personal computer to the Web site via the Internet. The Web site could verify the subscribers identity and then download the necessary executable software. Or, if a fast enough communications link is available, the Web server could implement the methods and transmit the associated images to the customer's personal computer. In preferred aspects of this embodiment, the methods of the present invention will be programmed using a computer programming language suited for network operation. For example, the Java programming language is particularly well suited.

The methods of the present invention are also well suited for implementation upon a television system. In a first television system embodiment capable of executing the methods of the present invention, a viewer may initiate and control the eye exercises at his or her convenience. For example, a viewer might decide to perform a few eye exercises during commercials. In some embodiments, the television channel would be monitored to determine whether the commercials are over, either prompting the viewer or automatically exiting the eye exercise program and returning to view the selected television channel.

In a second television system embodiment, a system of the present invention separate from the television set is coupled with the television set and operated as described above with respect to the first television embodiment. For example, the methods of the present invention are well suited for implementing within a standard video cassette recorder (VCR) for easy coupling with a television set.

It is further contemplated that some systems of the present invention will provide sophisticated training programs that gear themselves towards individual users. For example, in conjunction with performing exercises, a particular user might enter data such as name, date, current awareness eye fatigue and strain, and current physical state (e.g., just completed four hours of focused computer work, etc.). Based upon such data, the system will select, or recommend, an exercise program for the particular user. In addition, a history for the particular user may be maintained such the particular can track their progress. Further, the history may be utilized in selecting or recommending an exercise program.

The associated images may be moved in any suitable manner that promotes relief of eye strain and fatigue. While the embodiment described above discussed separating the associated images along a horizontal axis with respect to the viewer, the motion need not be constrained to such an axis. For example, the associated images may move upwards simultaneous with being separated. Or, the associated images may synchronously move about the viewing field, causing the eyes to track them, thereby exercising the eyes.

The present examples are to be considered as illustrative and not restrictive, and the invention is not to be limited to the details given herein, but may be modified within the scope of the appended claims.

What is claimed is:

1. A method for relieving eye strain of a viewer's eyes, the method comprising the
    (a) displaying a singular merged image on a display screen;
    (b) gradually and at a constant rate separating two associated images out of said merged image, increasing the size and the separation distance between the two associated images along a horizontal line, whereby, when a viewer focuses on a central focal point interposed between the viewer's eyes and the separated associated images, the viewer perceives, in addition to the associated images, a merged image derived from the associated images and the sensation of becoming nearer to the associated images;
    (c) stopping the lateral separation movement and increase in size of the associated images;
    (d) gradually and at a constant rate reducing the size and the lateral separation distance of the associated images until the associated images have become a singular merged image;
    (e) receiving an input indicating that the viewer no longer perceives the merged image;
    (f) stopping the movement of the associated images in response to the input indicating that the viewer no longer perceives the merged image; and
    (g) providing the viewer statistical information regarding the eye exercise in response to receiving the input indicating that the viewer no longer perceives the merged image.

2. A method as recited in claim 1 wherein the statistical information is derived from present results of the method and a history of past eye exercises performed by the viewer.

3. A method as recited in claim 1 wherein the associated images each have multiple objects.

4. A method as recited in claim 1 wherein the merged image has multiple objects.

5. A method as recited in claim 1 wherein the associated images have no objects in common.

6. A method as recited in claim 1 wherein the associated images have at least one object in common.

7. A method as recited in claim 1 wherein the associated images have objects related to each other such that the merged image is perceived by the viewer as having three dimensional characteristics.

8. A method as recited in claim 1 further including an initialization step wherein the viewer is allowed to select parameters that define, in part, the nature of a specific eye exercise to be performed.

9. A method as recited in claim 8 wherein the initialization step allows the viewer to pre-select a speed of motion for the step of moving the associated images.

10. A method as recited in claim 8 wherein the initialization step allows the viewer to define an initial value for the lateral separation distance.

11. A method as recited in claim 8 wherein the viewer may select a level of difficulty for a specific eye exercise to be performed.

12. A method as recited in claim 11 wherein the viewer may select the associated images to be displayed.

13. A method as recited in claim 1 further including a step of providing the viewer assistance in locating the central focal point thereby making it easier for the viewer to focus on the central focal point.

14. A method as recited in claim 13 wherein the step of providing the viewer assistance in locating the central focal point includes the step of providing the viewer a free standing apparatus having a focal tip which may be positioned such that the focal tip intersects with the central focal point, thereby allowing the viewer to focus on the central focal point by focusing on the focal tip.

15. A method as recited in claim 14 wherein the free standing apparatus further includes a base and a telescopic stem, the telescopic stem having a number of sections that slide one inside of another thereby allowing the telescopic stem to extend and contract, the telescopic stem being attached to the base by way of a hinge thereby enabling the telescopic stem and the base to fold together, and the focal tip being located on a distal end of the telescopic stem with respect to the base.

16. A method as recited in claim 14 wherein the free standing apparatus is integrated into a mouse pointing device of a computer system.

17. A method as recited in claim 1 wherein the method is implemented upon a computer system, the display screen being a computer display screen coupled to the computer system, and the viewer is a user of the computer system.

18. A method as recited in claim 17 wherein steps a)–i) are defined as eye exercise steps and the method further includes the step of periodically querying the user whether the user desires to perform the exercise steps, and if so, performing the exercise steps.

19. A method as recited in claim 17 wherein the method is implemented as part of a display screen saver computer program.

20. A method as recited in claim 1 wherein the method is implemented upon a television system and the display screen is a television display screen.

21. A screen saver method executed upon a computer system having a display screen, the screen saver method comprising the computer controlled steps of:
 (a) in response to a first predefined event, executing a screen saver operable to decrease damage to the display screen; and
 (b) in response to a second predefined event, executing eye exercises and performing the following substeps of:
  (i) displaying a singular merged image on a display screen;
  (ii) gradually and at a constant rate separating two associated images out of said merged image, increasing the size and the separation distance between the two associated images along a horizontal line, whereby, when a viewer focuses on a central focal point interposed between the viewer's eyes and the separated associated images, the viewer perceives, in addition to the associated images, a merged image derived from the associated images and the sensation of becoming nearer to the associated images;
  (iii) stopping the lateral separation movement and increase in size of the associated images;
  (iv) gradually and at a constant rate reducing the associated images' size and the lateral separation distance between the associated images until the associated images have become a singular merged image;
  (v) receiving an input indicating that the viewer no longer perceives the merged image;
  (vi) stopping the movement of the associated images in response to said input indicating that the viewer no longer perceives the merged image; and
  (vii) providing the viewer statistical information regarding the eye exercise in response to receiving the input indicating that the viewer no longer perceives the merged image.

22. A method as recited in claim 21 wherein the first predefined event is the passing of a certain period of time without the user providing input to the computer system.

23. A method as recited in claim 22 wherein the second predefined event is the user providing input to the computer system.

24. A method as recited in claim 21 wherein the statistical information is derived from present results of the method and a history of past eye exercises performed by the viewer.

25. A system for relieving eyestrain of a viewer's eyes, the system comprising:
 a central processing unit (CPU);
 random access memory (RAM) coupled with the CPU;
 read only memory (ROM) coupled with the CPU;
 a display screen coupled with the CPU;
 an input device coupled with the CPU whereby a viewer may enter data into the system; and
 an eye exercise application implemented on the computer system, the eye exercise application operable to display a single merged image on the display screen, gradually and at a constant rate separating two associated images out of said merged image and increasing the size and lateral separation distance of the two associated images along a horizontal line, whereby when a viewer focuses on a central focal point interposed between the viewer's eyes and the associated images, the viewer perceives, in addition to the associated images, a merged image derived from the associated images and the sensation of becoming nearer to the displayed objects, and the eye exercise application further operable both to receive an input indicating that the viewer no longer perceives the merged image.

26. A system as recited in claim 25 further comprising a free standing apparatus having a focal tip which may be positioned such that the focal tip intersects with the central focal point, thereby allowing the viewer to focus on the central focal point by focusing on the focal tip.

27. A system as recited in claim 26 wherein the free standing apparatus further includes a base and a telescopic stem, the telescopic stem having a number of sections that slide one inside of another thereby allowing the telescopic stem to extend and contract, the telescopic stem being attached to the base by way of a hinge thereby enabling the telescopic stem and the base to fold together, the focal tip being located on a distal end of the telescopic stem with respect to the base.

28. A computer program stored on a computer readable medium, the computer program comprising computer executable instructions for:
 (a) displaying a singular merged image on a display screen;
 (b) gradually and at a constant rate separating two associated images out of said merged image, increasing the size and the separation distance between the two associated images along a horizontal line, whereby, when a viewer focuses on a central focal point interposed between the viewer's eyes and the separated associated images, the viewer perceives, in addition to the associated images, a merged image derived from the associated images and the sensation of becoming nearer to the associated images;
 (c) stopping the lateral separation movement and increase in size of the associated images;

(d) gradually and at a constant rate reducing the size and the lateral separation distance of the associated images until the associated images have become a singular merged image;

(e) receiving an input indicating that the viewer no longer perceives the merged image;

(f) stopping the movement of the associated images in response to the input indicating that the viewer no longer perceives the merged image; and (g) providing the viewer statistical information regarding the eye exercise in response to receiving the input indicating that the viewer no longer perceives the merged image.

29. A computer program as recited in claim 28 wherein the computer executable instructions are programmed in the Java software programming language.

30. A computer data signal embodied in a carrier wave and representing computer executable instructions for relieving eye strain of a viewer's eyes, the computer executable instructions comprising:

(a) displaying a singular merged image on a display screen;

(b) gradually and at a constant rate separating two associated images out of said merged image, increasing the size and the separation distance between the two associated images along a horizontal line, whereby, when a viewer focuses on a central focal point interposed between the viewer's eyes and the separated associated images, the viewer perceives, in addition to the associated images, a merged image derived from the associated images and the sensation of becoming nearer to the associated images;

(c) stopping the lateral separation movement and increase in size of the associated images (upon achieving a maximum separation distance);

(d) gradually and at a constant rate reducing the size and the lateral separation distance of the associated images until the associated images have become a singular merged image;

(e) moving the associated images in such a manner that the viewer's eyes are exercised;

(f) receiving an input indicating that the viewer no longer perceives the merged image;

(g) stopping the movement of the associated images in response to said input indicating that the viewer no longer perceives the merged image; and (h) providing the viewer statistical information regarding the eye exercise in response to receiving the input indicating that the viewer no longer perceives the merged image.

31. A computer data signal as recited in claim 30 wherein the computer executable instructions are coded in the Java software programming language.

32. A computer implemented exercise method for relieving eyestrain of a viewer's eyes, the exercise method comprising the computer controlled steps of:

(a) providing a viewer with an exercise setup screen wherein the viewer may select from a plurality of associated image pairs, the plurality of associated image pairs including an image pair having no common objects and an image pair having at least one common object;

(b) providing a viewer with an exercise setup screen wherein the viewer may input viewer's name;

(c) providing a viewer with an exercise setup screen wherein the viewer may input current date;

(d) providing a viewer with an exercise setup screen wherein the viewer may input viewer's level of eye fatigue and strain;

(e) providing a viewer with an exercise setup screen wherein the viewer may input regarding current physical state;

(f) processing viewer's recorded performance history and inputted data;

(g) recommending or selecting an exercise program;

(h) providing a viewer with an exercise setup screen wherein the viewer may input a selection of the desired image pair for use in implementing the exercise method;

(i) displaying a singular merged image on a display screen;

(j) gradually and at a constant rate separating two associated images out of said merged image, increasing the size and the separation distance between the two associated images along a horizontal line, whereby, when a viewer focuses on a central focal point interposed between the viewer's eyes and the separated associated images, the viewer perceives, in addition to the associated images, a merged image derived from the associated images and the sensation of becoming nearer to the associated images;

(k) stopping the lateral separation movement and increase in size of the associated images (upon achieving a maximum separation distance);

(l) gradually and at a constant rate reducing the size and the lateral separation distance of the associated images until the associated images have become a singular merged image;

(m) moving the associated images in such a manner that the viewer's eyes are exercised;

(n) receiving an input indicating that the viewer no longer perceives the merged image; and (o) stopping the movement of the associated images in response to receiving the input indicating that the viewer no longer perceives the merged image.

* * * * *